(12) United States Patent
Windheuser et al.

(10) Patent No.: US 6,606,515 B1
(45) Date of Patent: Aug. 12, 2003

(54) GUIDE WIRE INSERTION AND RE-INSERTION TOOLS AND METHODS OF USE

(75) Inventors: James E. Windheuser, Hopkinton, MA (US); James Yearick, Shrewsbury, MA (US); Oscar Carrillo, Jr., Attleboro, MA (US); Robert C. Allman, Wakefield, MA (US); Fernando Alvarez de Toledo, Concord, MA (US); Stephen C. Evans, Westford, MA (US); Norman C. May, Franklin, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/312,438

(22) Filed: May 14, 1999

Related U.S. Application Data

(63) Continuation-in-part of application No. 09/080,520, filed on May 18, 1998, now Pat. No. 6,096,009, which is a continuation-in-part of application No. 08/926,200, filed on Sep. 9, 1997, now Pat. No. 6,007,522.
(60) Provisional application No. 60/025,235, filed on Sep. 13, 1996.

(51) Int. Cl.[7] .............................................. A61M 25/00
(52) U.S. Cl. ....................................... 600/434; 600/585
(58) Field of Search ............................. 604/165.01, 53, 604/103.04, 117, 159, 165.04, 166.01, 208, 220, 523, 533, 535, 539; 600/434, 585

(56) References Cited

U.S. PATENT DOCUMENTS 1,204,053 A 11/1916 Moore
2,623,520 A 12/1952 Bamford, Jr. et al. ...... 128/221

(List continued on next page.)

FOREIGN PATENT DOCUMENTS

DE 41 15 007 A1 11/1992
EP 0 328 760 A2 8/1989

(List continued on next page.)

OTHER PUBLICATIONS

Knecht, Gregory L., M.D. et al., "Double-channel Fistulotome For Endoscopic Drainage of Pancreatic Pseudocyst", *Gastrointestinal Endoscopy*, vol. 37, No. 3, May/Jun. 1991, pp. 356–357.

(List continued on next page.)

*Primary Examiner*—Sharon Kennedy
(74) *Attorney, Agent, or Firm*—Crompton, Seager & Tufte, LLC

(57) ABSTRACT

An insertion tool and method for easily inserting a guide wire into a guide wire lumen of a catheter, particularly a rapid exchange catheter, for use in an endoscope. The insertion tool includes a main body having a main lumen and a funnel-shaped extension having a funnel lumen that merges with the main lumen. The funnel lumen has a first large opening and a second smaller opening aligned with the guide wire lumen of the catheter such that, when the catheter is disposed in the main lumen, the guide wire may be easily inserted into the large opening of the funnel-shaped extension and into the guide wire lumen of the catheter. The insertion tool may include a tongue or key disposed in the main lumen that is sized to fit in a slot of the catheter to thereby maintain alignment between the funnel lumen and the slot of the catheter. The insertion tool may alternatively include a non-round surface disposed in the main lumen that engages a non-round surface on the exterior of the catheter to thereby maintain alignment between the funnel lumen and the slot of the catheter. The insertion tool may further include a longitudinal slot in the funnel-shaped extension and/or main body to allow removal of the guide wire from the insertion tool while the guide wire remains in the guide wire lumen of the catheter.

11 Claims, 21 Drawing Sheets

U.S. PATENT DOCUMENTS

| | | | | |
|---|---|---|---|---|
| 3,015,869 | A | 1/1962 | Rapata | 24/213 |
| 3,536,281 | A | 10/1970 | Meehan et al. | 248/73 |
| RE31,855 | E | 3/1985 | Osborne | 604/161 |
| 4,696,668 | A | 9/1987 | Wilcox | 604/28 |
| 4,748,982 | A | 6/1988 | Horzewski et al. | 128/344 |
| 4,762,129 | A | 8/1988 | Bonzel | 606/194 |
| 4,771,777 | A | 9/1988 | Horzewski et al. | 128/344 |
| 4,781,677 | A | 11/1988 | Wilcox | 604/28 |
| 4,835,824 | A | 6/1989 | Durham et al. | 24/339 |
| 4,844,092 | A | 7/1989 | Rydell et al. | 128/772 |
| 4,900,184 | A | 2/1990 | Cleveland | 403/397 |
| 4,905,667 | A | 3/1990 | Foerster et al. | 128/4 |
| 4,917,103 | A | 4/1990 | Gambale et al. | 128/772 |
| 4,927,418 | A | 5/1990 | Dake et al. | 604/264 |
| 4,928,693 | A | 5/1990 | Goodin et al. | 128/637 |
| 4,946,443 | A | 8/1990 | Hauser et al. | 604/165 |
| 4,973,329 | A * | 11/1990 | Park et al. | 606/1 |
| 4,983,168 | A | 1/1991 | Moorehead | 604/161 |
| 4,988,356 | A * | 1/1991 | Crittenden et al. | 606/192 |
| 4,997,421 | A | 3/1991 | Palsrok et al. | 604/174 |
| 5,040,548 | A | 8/1991 | Yock | 128/898 |
| 5,061,273 | A | 10/1991 | Yock | 606/194 |
| 5,064,414 | A | 11/1991 | Revane | 604/165 |
| 5,125,915 | A | 6/1992 | Berry et al. | 604/283 |
| 5,135,535 | A | 8/1992 | Kramer | 606/194 |
| 5,139,032 | A * | 8/1992 | Jahrmarkt et al. | 128/772 |
| 5,147,377 | A | 9/1992 | Sahota | 606/194 |
| 5,158,545 | A | 10/1992 | Trudell et al. | 604/53 |
| 5,167,634 | A | 12/1992 | Corrigan, Jr. et al. | 604/160 |
| 5,191,888 | A * | 3/1993 | Palmer et al. | 128/657 |
| 5,195,978 | A | 3/1993 | Schiffer | 604/161 |
| 5,205,822 | A | 4/1993 | Johnson et al. | 604/96 |
| 5,232,445 | A | 8/1993 | Bonzel | 604/96 |
| 5,248,306 | A | 9/1993 | Clark et al. | 604/283 |
| 5,250,033 | A | 10/1993 | Evans et al. | 604/160 |
| 5,279,562 | A | 1/1994 | Sirhan et al. | 604/96 |
| 5,282,479 | A | 2/1994 | Havran | 128/772 |
| 5,290,232 | A | 3/1994 | Johnson et al. | 604/96 |
| 5,290,241 | A | 3/1994 | Kraus et al. | 604/161 |
| 5,300,085 | A | 4/1994 | Yock | 606/191 |
| 5,306,247 | A | 4/1994 | Pfenninger | 604/96 |
| 5,308,318 | A | 5/1994 | Plassche, Jr. | 604/54 |
| 5,320,602 | A | 6/1994 | Karpiel | 604/54 |
| 5,324,259 | A | 6/1994 | Taylor et al. | 604/96 |
| 5,324,269 | A | 6/1994 | Miraki | 604/160 |
| 5,334,143 | A | 8/1994 | Carroll | 604/54 |
| 5,334,187 | A | 8/1994 | Fischell et al. | 604/194 |
| 5,350,395 | A | 9/1994 | Yock | 606/194 |
| 5,364,355 | A | 11/1994 | Alden et al. | 604/96 |
| 5,370,623 | A | 12/1994 | Kreamer | 604/165 |
| 5,389,087 | A | 2/1995 | Miraki | 604/247 |
| 5,397,302 | A | 3/1995 | Weaver et al. | 604/54 |
| 5,448,993 | A * | 9/1995 | Lynch et al. | 128/657 |
| 5,451,233 | A | 9/1995 | Yock | 606/194 |
| 5,454,790 | A | 10/1995 | Dubrul | 604/104 |
| 5,456,284 | A * | 10/1995 | Ryan et al. | 137/522 |
| 5,458,584 | A | 10/1995 | Ginn et al. | 604/280 |
| 5,480,389 | A | 1/1996 | McWha et al. | 604/165 |
| 5,489,271 | A | 2/1996 | Andersen | 604/102 |
| 5,490,837 | A | 2/1996 | Blaeser et al. | 604/96 |
| 5,496,346 | A | 3/1996 | Horzewski et al. | 606/154 |
| 5,501,227 | A | 3/1996 | Yock | 128/662.06 |
| 5,531,700 | A | 7/1996 | Moore et al. | 604/164 |
| 5,536,248 | A | 7/1996 | Weaver et al. | 604/54 |
| 5,540,236 | A | 7/1996 | Ginn | 128/772 |
| 5,599,299 | A | 2/1997 | Weaver et al. | 604/54 |
| 5,599,300 | A | 2/1997 | Weaver et al. | 604/54 |
| 5,626,600 | A | 5/1997 | Horzewski et al. | 606/194 |
| 5,706,827 | A | 1/1998 | Ehr et al. | 128/772 |
| 5,725,504 | A | 3/1998 | Collins | 604/165 |
| 5,788,681 | A | 8/1998 | Weaver et al. | 604/280 |
| 5,800,414 | A | 9/1998 | Cazal | 604/280 |
| 5,833,706 | A | 11/1998 | St. Germain et al. | 606/194 |
| 5,843,028 | A | 12/1998 | Weaver et al. | 604/54 |
| 5,849,016 | A | 12/1998 | Suhr | 606/108 |
| 5,921,971 | A | 7/1999 | Agro et al. | 604/280 |
| 5,935,114 | A * | 8/1999 | Jang et al. | 604/264 |
| 5,978,699 | A * | 11/1999 | Fehse et al. | 600/434 |
| 6,190,333 | B1 * | 2/2001 | Valencia | 600/585 |
| 6,277,100 | B1 * | 8/2001 | Raulerson et al. | 604/212 |

FOREIGN PATENT DOCUMENTS

| | | |
|---|---|---|
| EP | 0 388 112 A2 | 9/1990 |
| EP | 0 792 657 A2 | 9/1997 |
| EP | 0 801 955 B1 | 3/1999 |
| WO | WO 92/03963 | 3/1992 |
| WO | WO 96/33764 | 10/1996 |
| WO | WO 98/10820 | 3/1998 |
| WO | WO 98/10-821 | 3/1998 |

OTHER PUBLICATIONS

Siegel, Jerome H., M.D. et al., "Two New Methods For Selective Bile Duct Cannulation and Sphincterotomy", *Gastrointestinal Endoscopy*, vol. 33, No. 6, Dec. 1987, pp. 438–440.

* cited by examiner

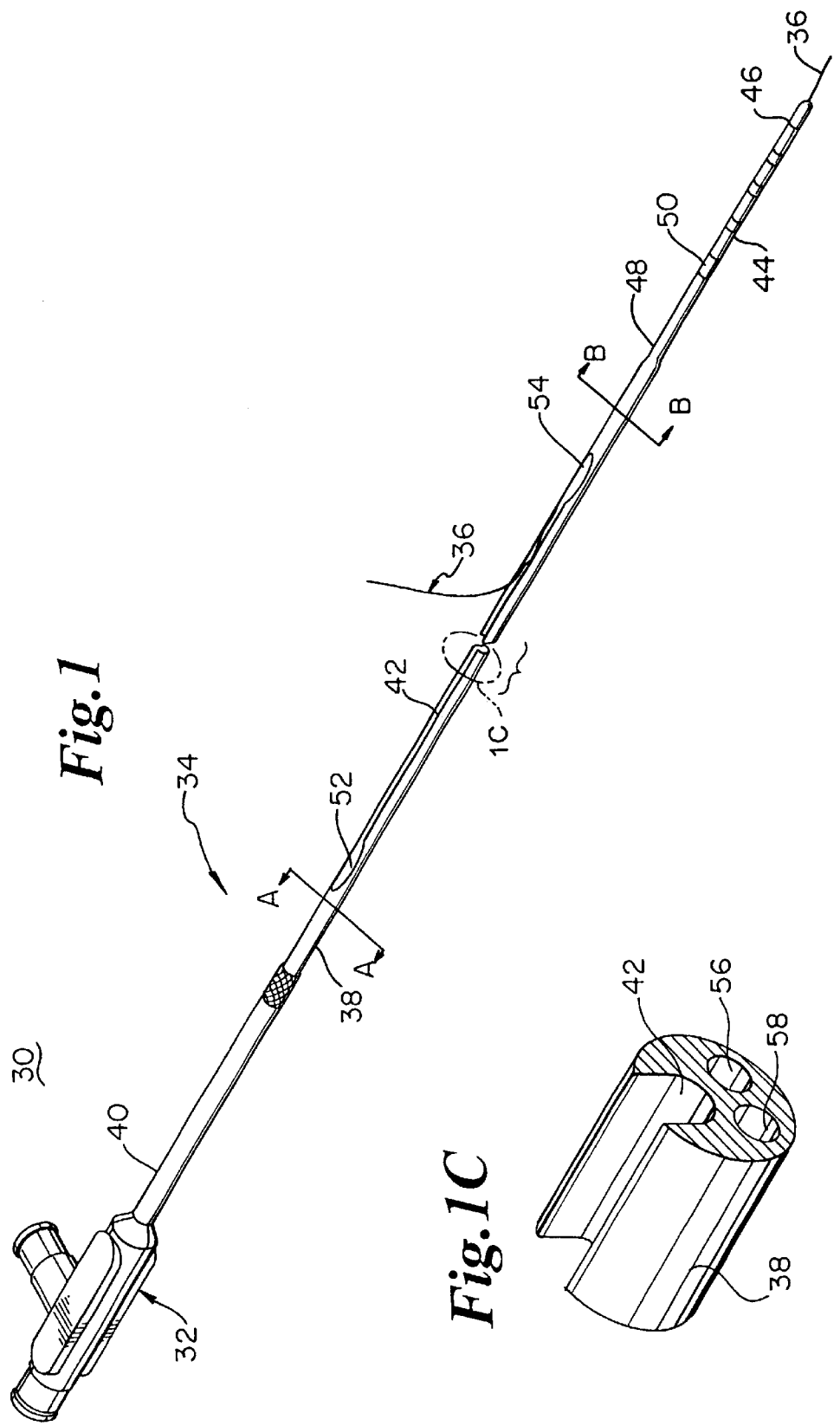

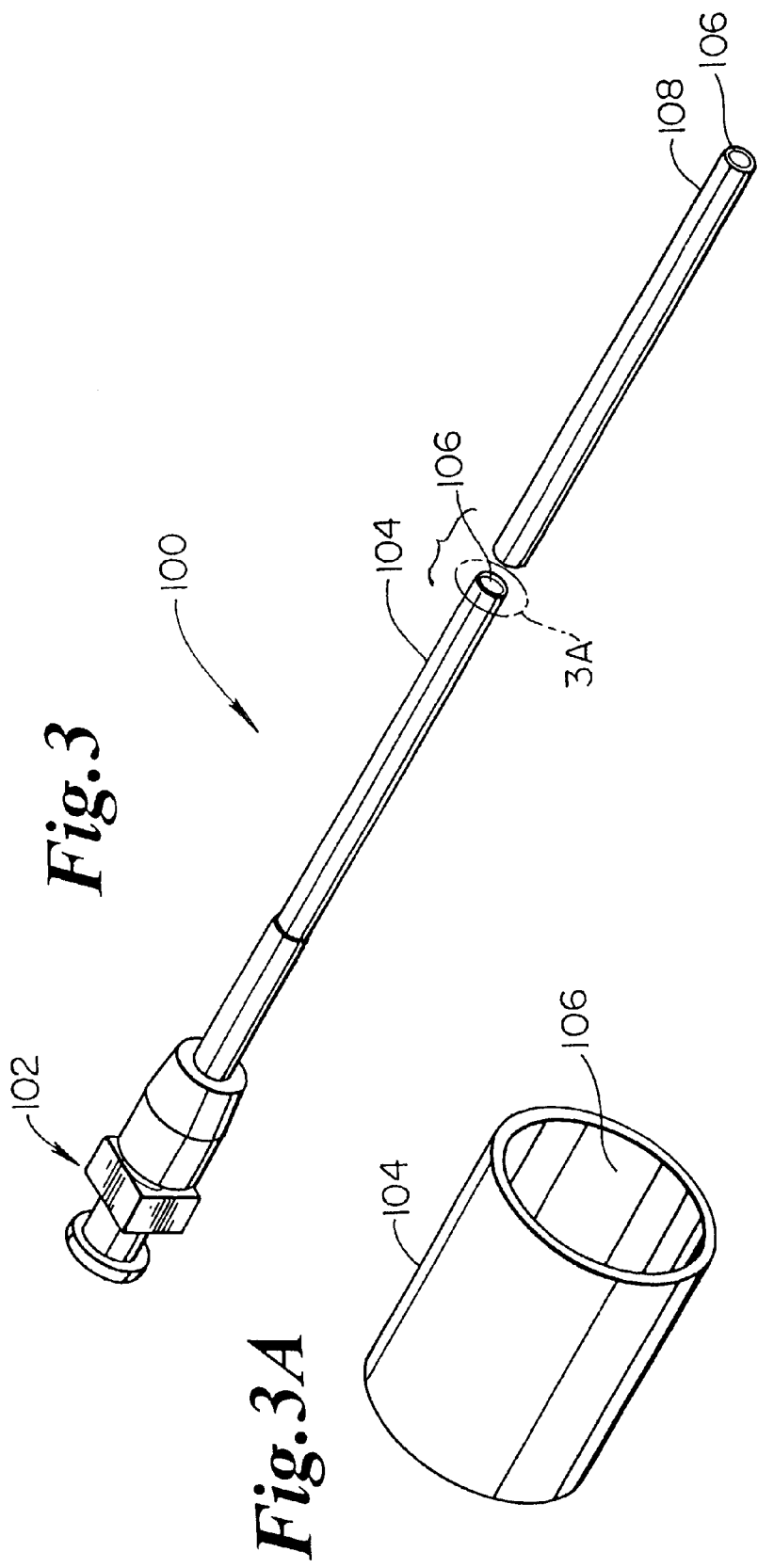

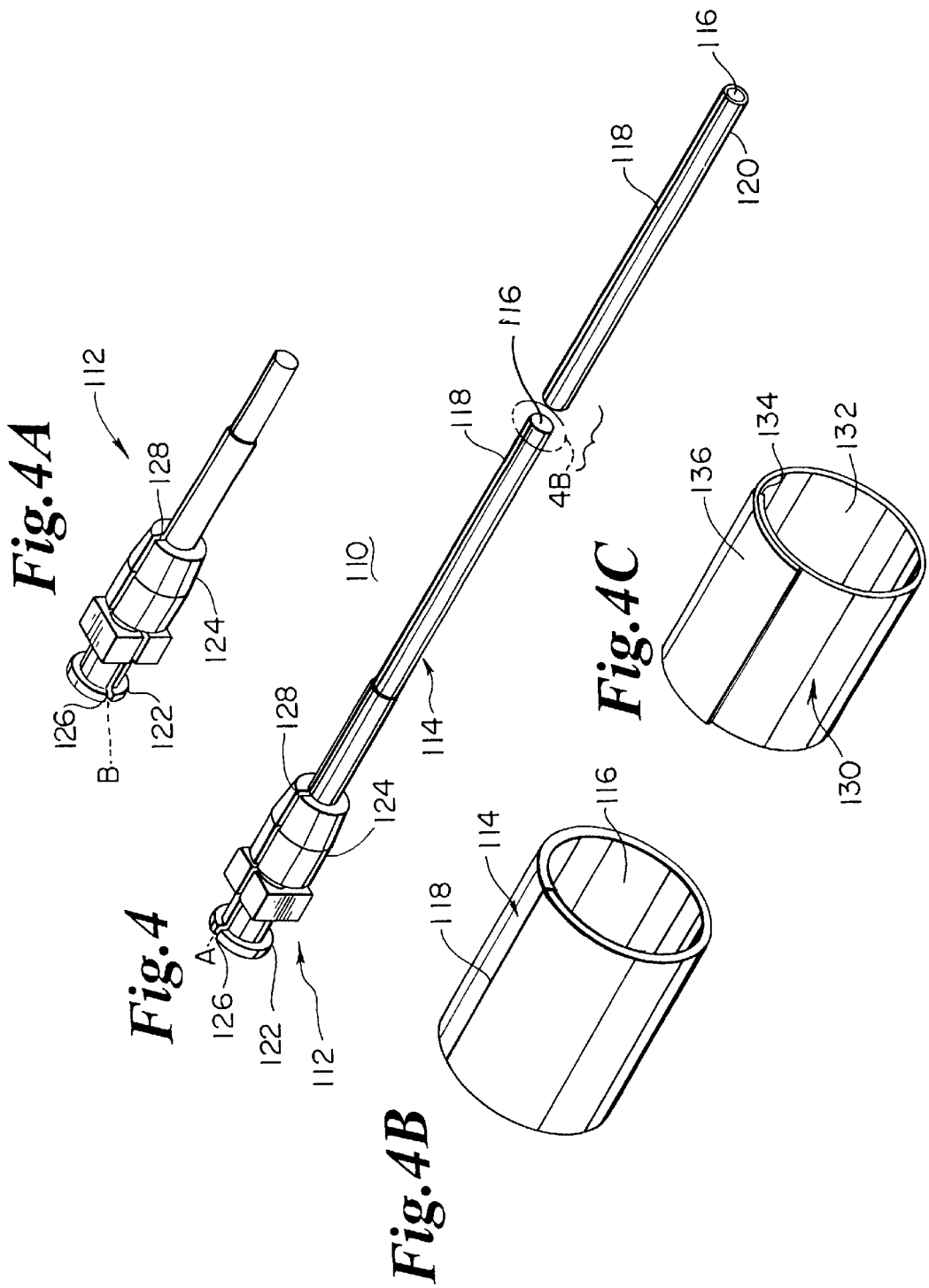

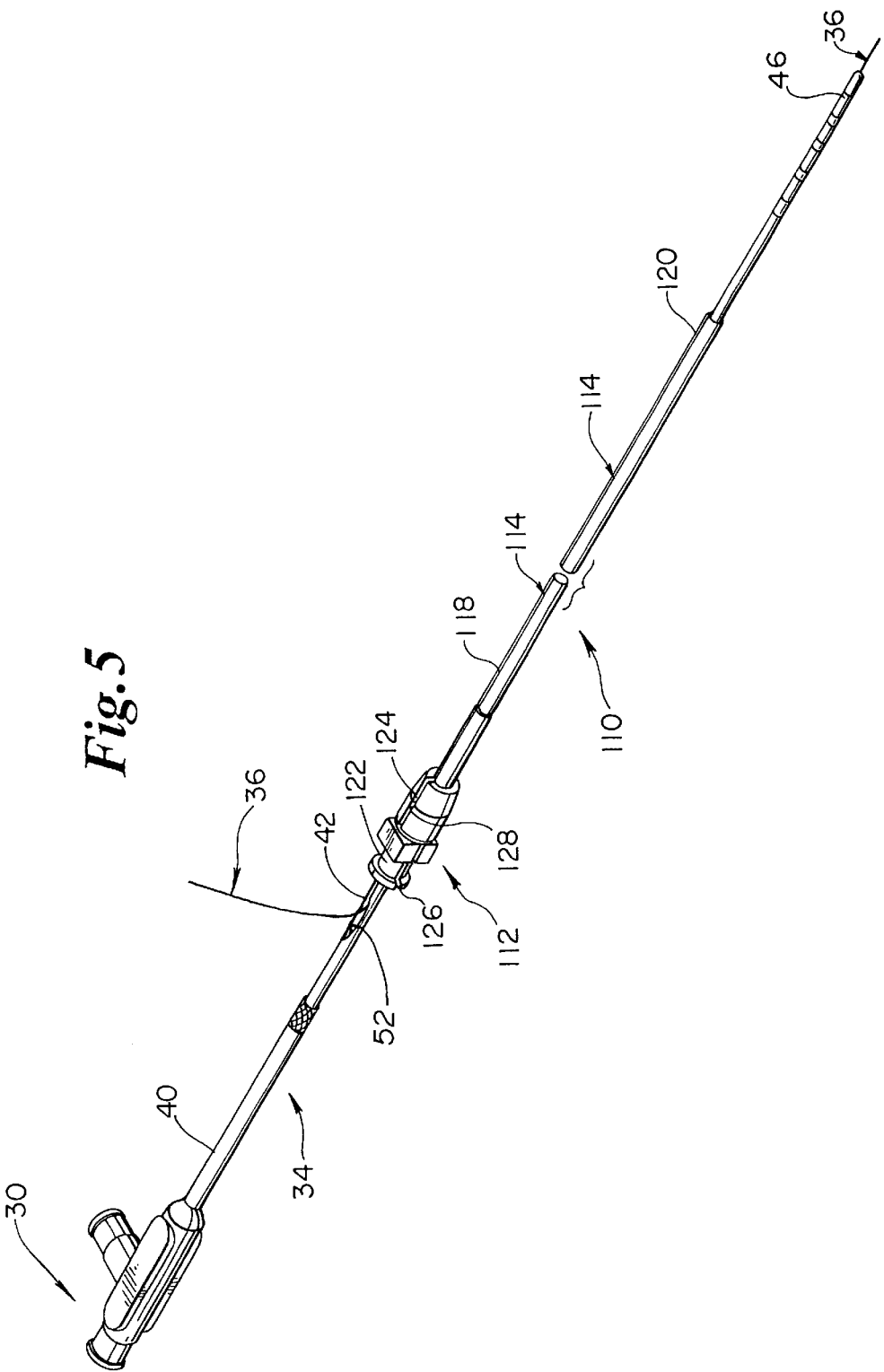

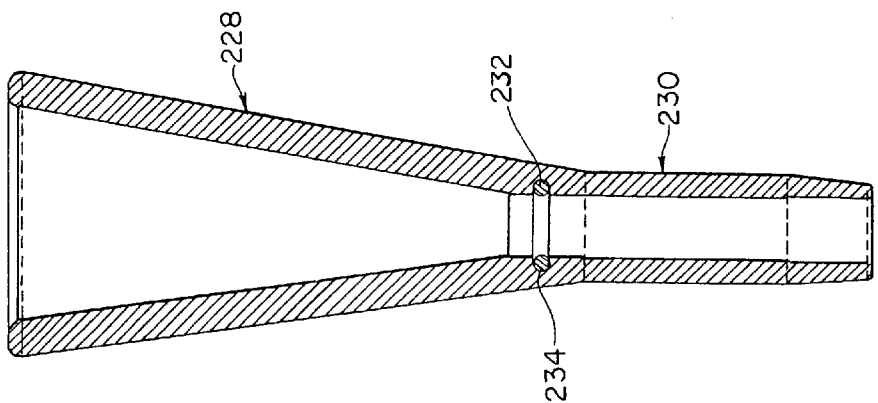
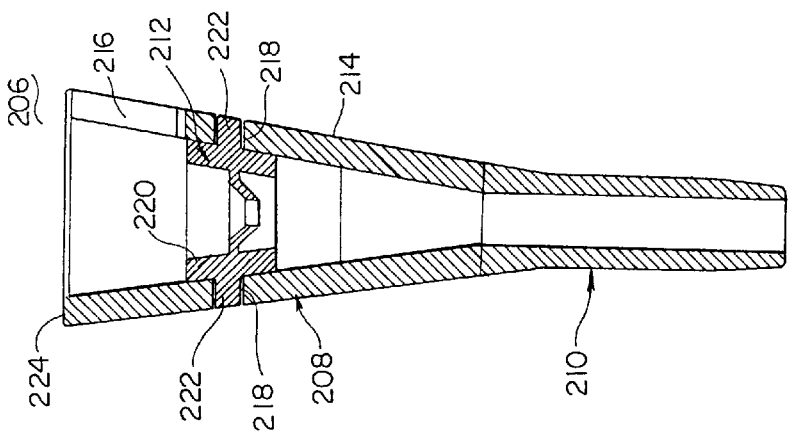
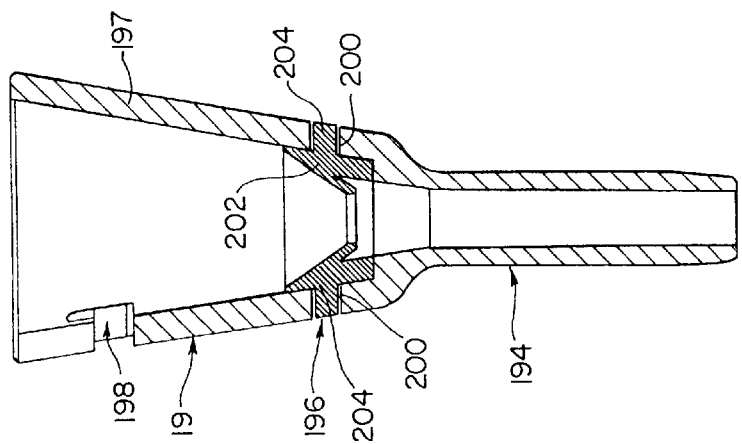

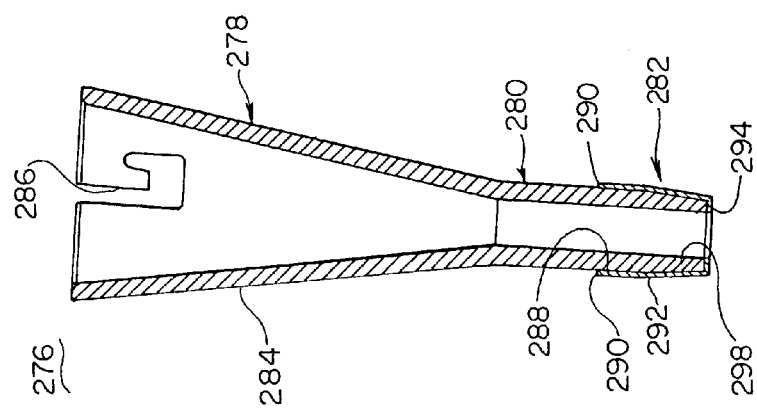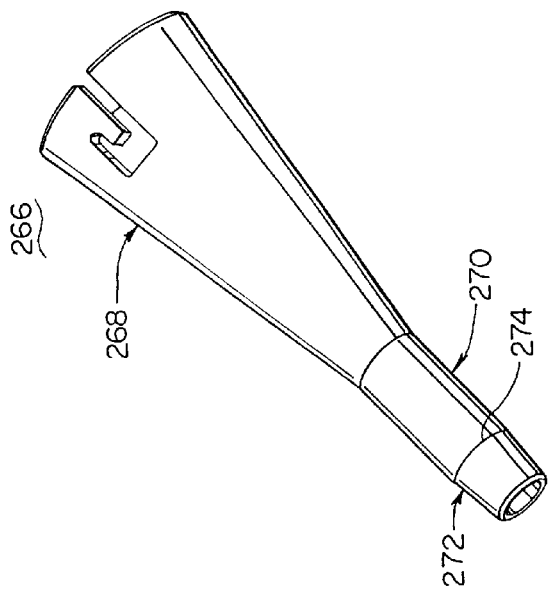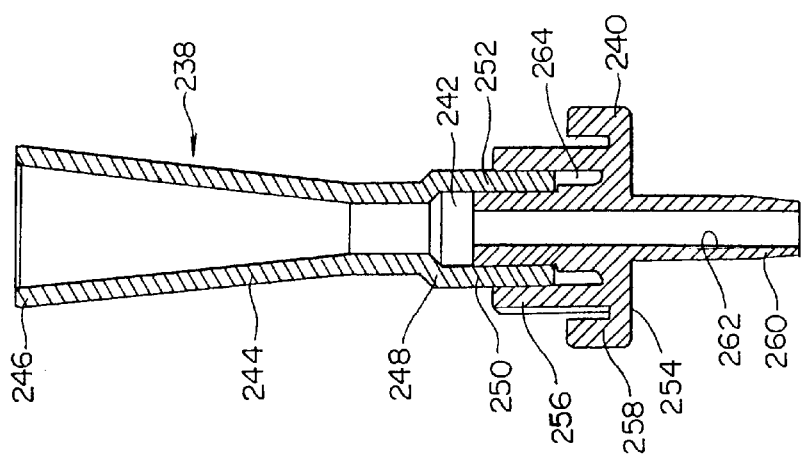

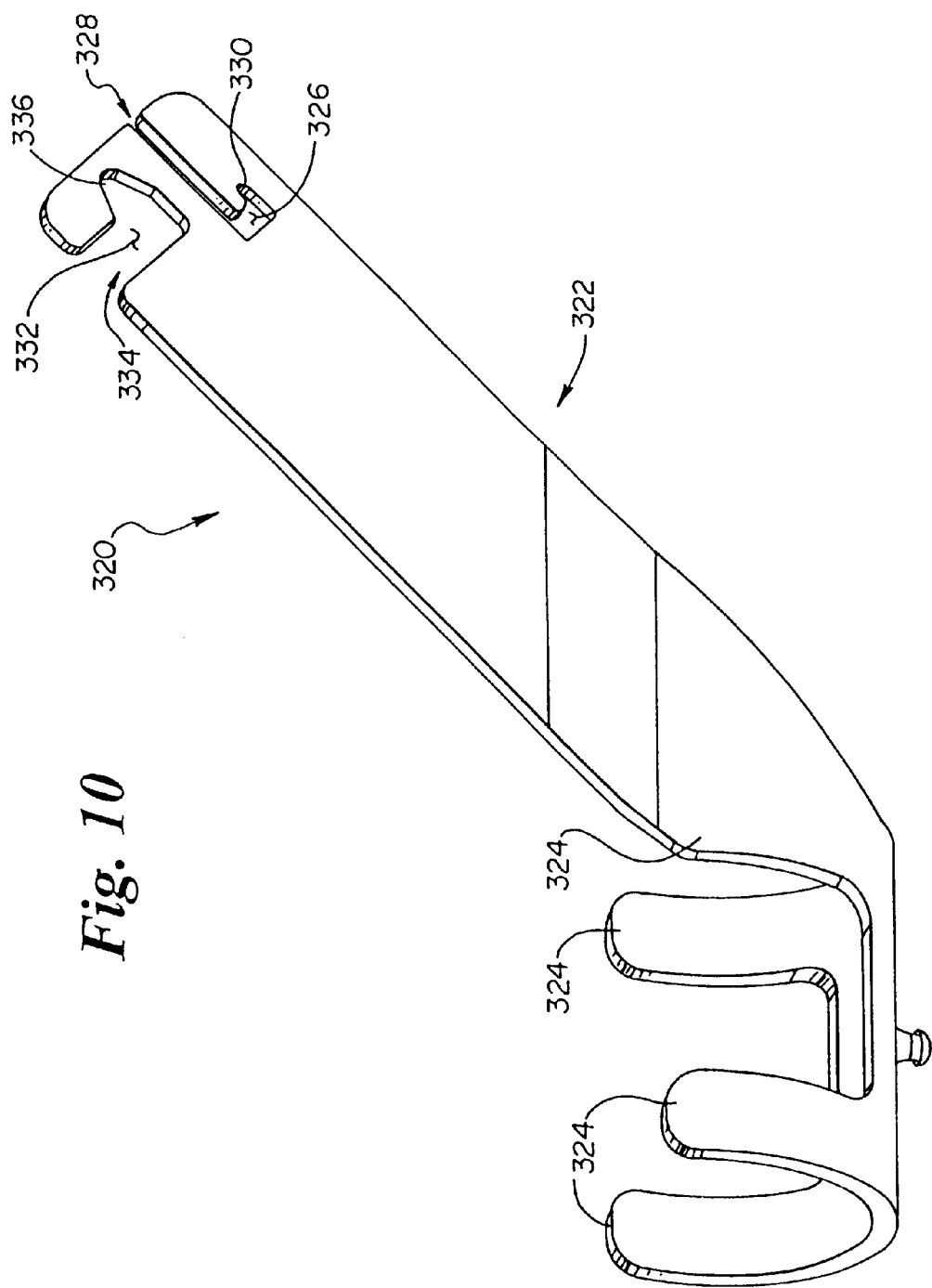

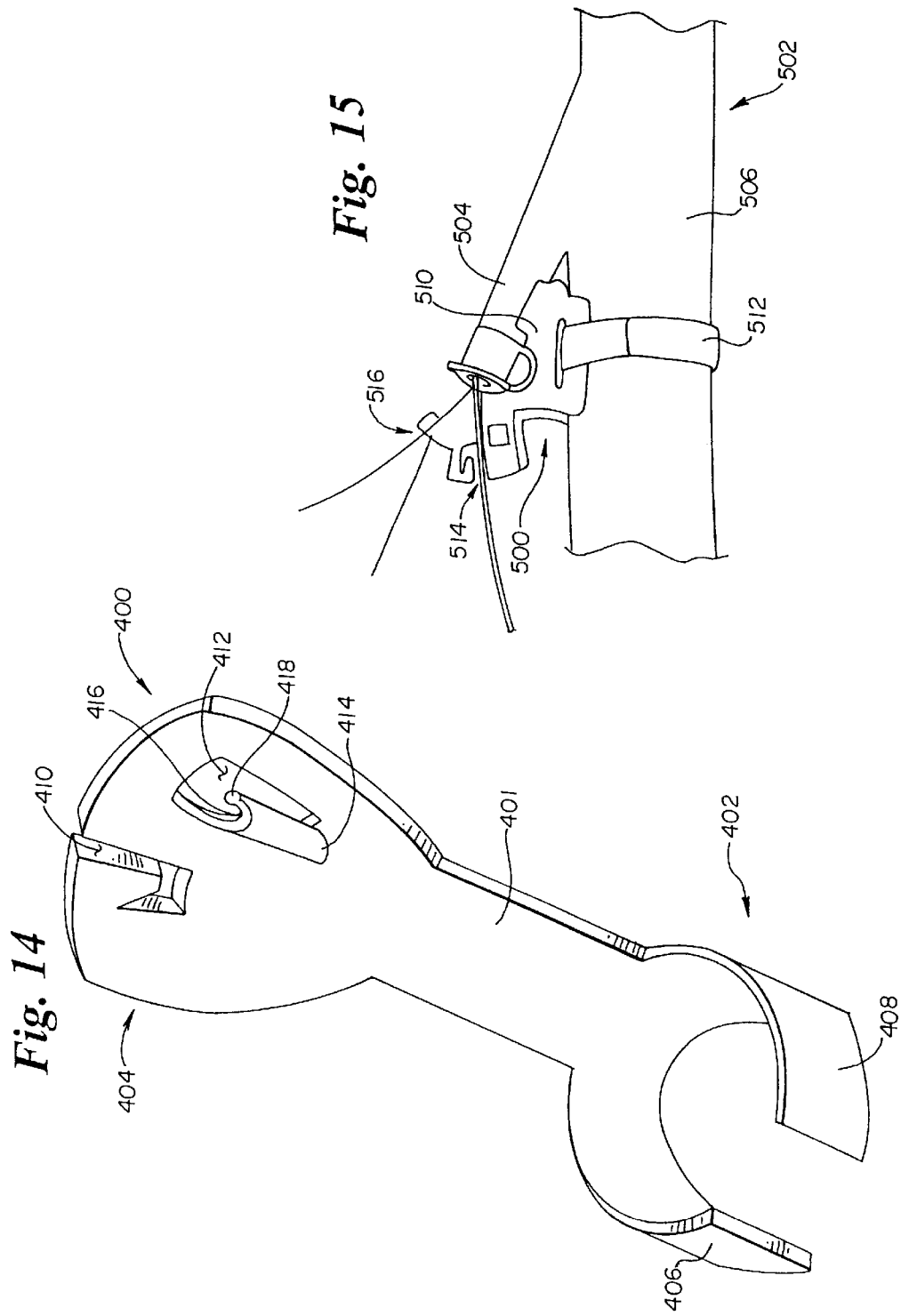

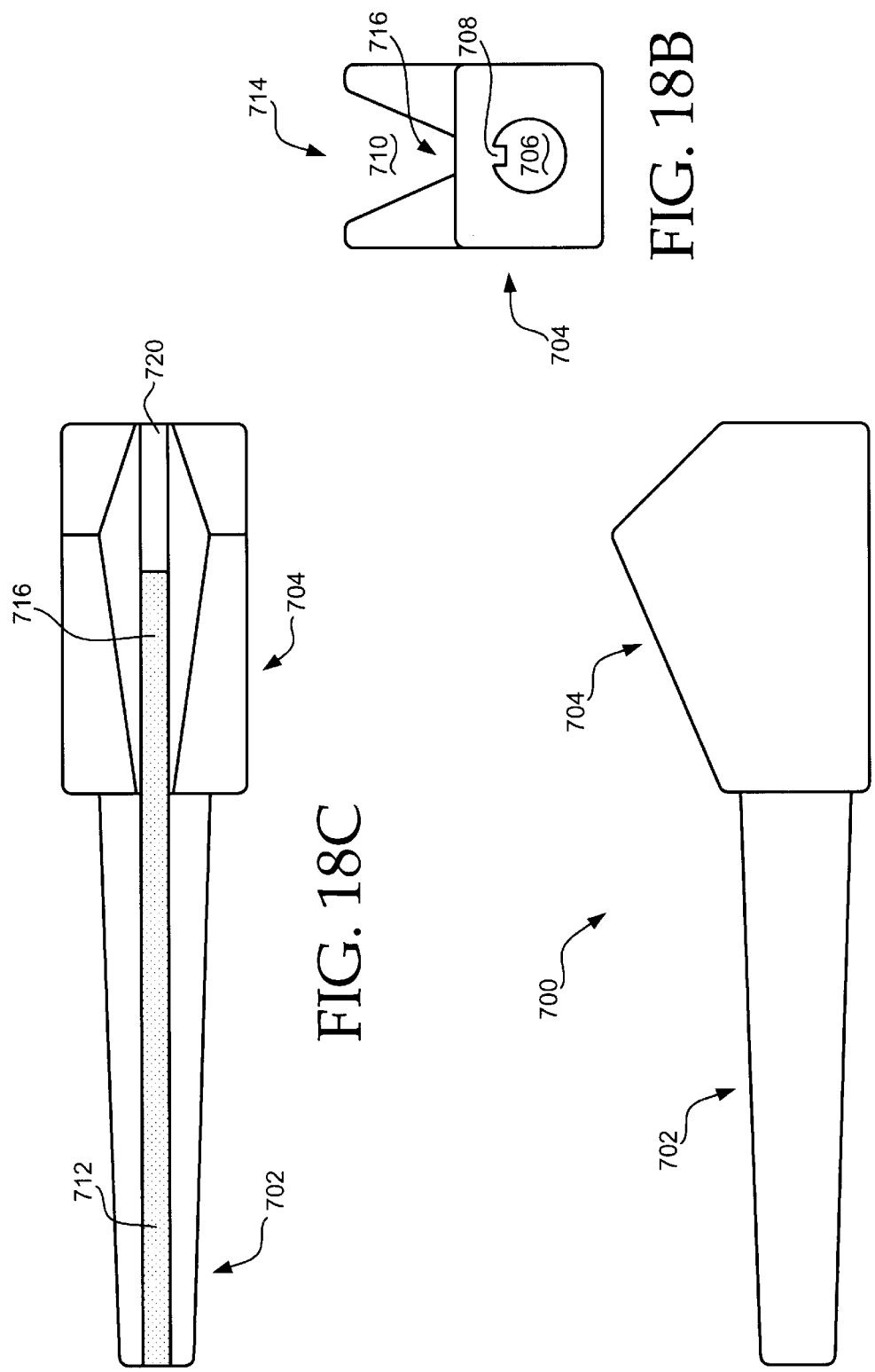

*Fig. 19*
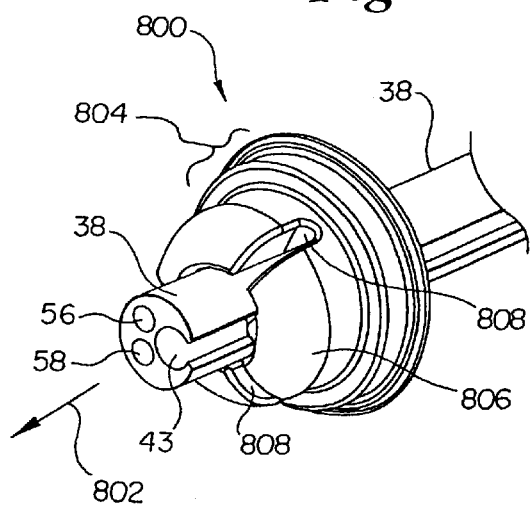
*Fig. 20A* *Fig. 20B* *Fig. 20C*
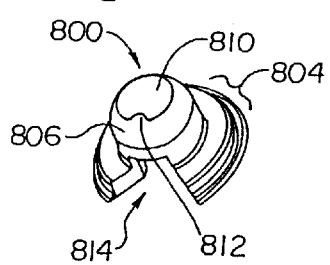 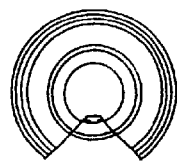 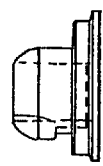
*Fig. 20D* *Fig. 20E* *Fig.20F*
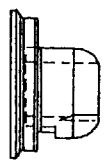 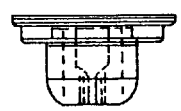 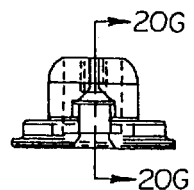
*Fig.20G*
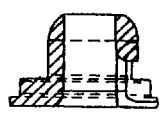

GUIDE WIRE INSERTION AND RE-INSERTION TOOLS AND METHODS OF USE

CROSS REFERENCE TO RELATED APPLICATIONS

This application is a continuation-in-part application of U.S. patent application Ser. No. 09/080,520, filed on May 18, 1998, now U.S. Pat. No. 6,096,009 issued on Aug. 1, 2000, entitled "Guide wire and Catheter Locking Device and Method"; which is a continuation-in-part application of U.S. patent application Ser. No. 08/926,200, filed on Sep. 9, 1997, now U.S. Pat. No. 6,007,522 issued on Dec. 28, 1999, entitled "Single Operator Exchange Biliary Catheter"; which claims priority to U.S. Provisional Application No. 60/025,235, filed Sep. 13, 1996, entitled "Single Operator Exchange Biliary Catheter", the entire disclosures of which are hereby incorporated by reference. This application is related to concurrently filed U.S. patent application Ser. No. 09/312,340, filed on May 14, 1999, now U.S. Pat. No. 6,346,093 issued on Feb. 12, 2002, entitled "Single Operator Exchange Biliary Catheter With Common Distal Lumen", which is hereby incorporated by reference.

FIELD OF THE INVENTION

The present invention generally relates to endoscopic devices and methods of use. Specifically, the present invention relates to catheters for use in combination with guide wires and endoscopes.

BACKGROUND OF THE INVENTION

Endoscopic procedures for treating abnormal pathologies within the alimentary canal system and biliary tree (including the biliary, hepatic, and pancreatic ducts) are increasing in number. The endoscope provides access to the general area of a desired duct using direct visualization. However, the duct itself must be navigated using a catheter in conjunction with fluoroscopy and guide wires.

Catheters are known for treatment of targeted anatomical regions. Known methods and devices for using biliary catheters for accessing the biliary tree for performing catheter procedures are disclosed in Weaver et al., U.S. Pat. No. 5,397,302 and Karpiel, U.S. Pat. No. 5,320,602, the disclosures of which are herein incorporated by reference. In general, for treatment of an abnormal pathology within a patient's biliary tree, an endoscope is first introduced into the mouth of the patient. The endoscope includes a proximal end and a distal end, and has a lumen extending longitudinally between the proximal and distal ends. The endoscope is guided through the patient's alimentary tract or canal until an opening at the distal end of the endoscope is proximate the area to receive treatment. At this point, the endoscope allows other components, such as a catheter, to access the targeted area.

For visualization or treatment within the biliary tree, the distal end of the endoscope is positioned proximate to the papilla of vater leading to the common bile duct and the pancreatic duct. A catheter is guided through the lumen of the endoscope until a distal tip of the catheter emerges from the opening at the distal end of the endoscope.

The catheter may be used for accessing the biliary tree. The distal end of the catheter is guided through the orifice to the papilla of vater (located between the sphincter of oddi) leading to the common bile duct and the pancreatic duct. A guide wire may be used in conjunction with the catheter to facilitate accessing a desired location within the biliary tree. The guide wire is inserted in an opening at a proximal end of the catheter and guided through the catheter until it emerges from the distal end of the catheter.

If visualization of the common bile duct is desired, the guide wire is guided into the common bile duct. The catheter is advanced over the guide wire, as previously described, until the distal end of the catheter is positioned in the common bile duct at the desired location. The catheter is now in position for delivery of contrast media for fluoroscopic visualization of anatomical detail within the common bile duct.

Visualization may reveal selected areas within the common bile duct that require treatment. To treat the selected areas, a different catheter is typically required, necessitating a catheter exchange. A catheter exchange typically involves removing the first catheter from the endoscope over the guide wire, and advancing a second catheter over the guide wire to the desired treatment site. Thus, once the guide wire is in place relative to the targeted area, it is highly desirable to maintain the position of the guide wire during subsequent catheter procedures, including during a catheter exchange procedure. If the guide wire moves during such a procedure, the guide wire may have to be re-directed through the body ducts to the target site, which is often a difficult, time consuming, and tedious task.

In addition to performing a catheter exchange procedure, it may also be desirable to perform a guide wire exchange procedure. This may be desirable when, for example, a first guide wire is too large to fit through a desired body duct, or otherwise lacks the desired characteristics. Under these circumstances, a physician may leave the catheter in place, withdraw the first guide wire from the catheter, and insert a second guide wire through the catheter to the desired site. During this procedure, the catheter guides the guide wire to the desired site. Thus, once the catheter is positioned at a target site, it is highly desirable to maintain the position of the catheter during a guide wire exchange procedure so that the second guide wire may be guided directly to the desired site in a minimum amount of time.

To maintain the position of a guide wire and/or catheter, a physician typically must grasp the proximal end of the guide wire and/or catheter with one hand, and perform the corresponding exchange with the other. This is difficult and often results in the movement of the guide wire and/or catheter. Therefore, it would be desirable to provide a locking device whereby the physician can secure the position of the guide wire and/or catheter during an exchange procedure, thereby freeing both hands to perform other tasks.

It would also be desirable to have a tool for inserting a guide wire into a catheter. Inserting a guide wire into the guide wire lumen of a rapid exchange catheter, whether in preparing the catheter and guide wire for insertion into the endoscope or performing a guide wire exchange procedure, is often difficult due to the relatively small size of the guide wire entry slot or port. Specifically, the guide wire entry slot or port may be difficult to locate on the catheter shaft and, even after the guide wire slot or port has been located, inserting the guide wire into the guide wire lumen may be as difficult as threading a needle. Accordingly, it would be desirable to have a tool and method for assisting in the insertion of a guide wire into a catheter, particularly a rapid exchange catheter.

SUMMARY OF THE INVENTION

The present invention provides an insertion tool and method for easily inserting a guide wire into a catheter, particularly a rapid exchange catheter, for use in an endoscope. An insertion tool in accordance with an embodiment of the present invention includes a main body having a lumen sized to accommodate the catheter and a funnel-shaped extension having a funnel-shaped lumen that merges with the main lumen. The funnel-shaped lumen has a large first opening and a smaller second opening aligned with the guide wire lumen of the catheter such that, when the catheter is disposed in the main lumen, the guide wire may be easily inserted into the large opening of the funnel-shaped lumen and into the guide wire lumen of the catheter.

The catheter, as in a rapid exchange catheter, may include a longitudinal slot that provides access to the guide wire lumen, in which case the insertion tool may include a corresponding tongue or key disposed in the main lumen. Alternatively, the insertion tool may include a non-round (e.g., flat) surface that engages a similar surface on the catheter. The tongue or engaging surface is aligned with the funnel-shaped extension and the slot of the catheter to thereby maintain alignment between the funnel-shaped lumen and the slot. The insertion tool may also include a longitudinal slot in the funnel and/or main body that is aligned with the longitudinal slot of the catheter to allow removal of the guide wire from the insertion tool while the guide wire remains disposed in the guide wire lumen of the catheter.

A method of using an insertion tool in accordance with an embodiment of the present invention includes the steps of placing the insertion tool on the catheter such that the catheter extends through the main lumen and inserting the guide wire through the funnel-shaped extension of the insertion tool and into the guide wire lumen of the catheter. The insertion tool may be slidable or stationary on the catheter. If the insertion tool is slidable on the catheter, the insertion tool may be advanced along the catheter to insert a section of thereof securely into the lumen of the endoscope, preferably prior to inserting the guide wire. The section may be inserted a sufficient distance to open the valve in the lumen of the endoscope to permit unhindered longitudinal movement of the catheter through the valve. After the guide wire has been inserted into the guide wire lumen of the catheter, the guide wire may be removed from the insertion tool through a slot in the funnel-shaped extension and/or main body while the guide wire remains in place within the catheter. The insertion tool may then be removed from the lumen of the endoscope by sliding the tool proximally along the catheter.

The present invention also provides a re-insertion tool and method for re-inserting a guide wire into a channel of a catheter. The re-insertion tool is particularly useful in combination with an endoscope and a SOE catheter disposed therein. Because the endoscope may be too small to accommodate the guide wire and the catheter side-by-side, it is desirable to reintroduce the guide wire into the channel of the catheter proximal of the port of the endoscope, before advancing or retracting the catheter and/or guide wire. Specifically, with the distal portion of the guide wire disposed in the channel/guide wire lumen of the catheter distal of the port of the endoscope, and the proximal portion of the guide wire disposed adjacent to the catheter proximal of the port, the re-insertion tool may be used to re-introduce the guide wire into the channel of the catheter proximal of the port. The re-insertion tool thereby facilitates easy retraction and advancement of the catheter and/or guide wire relative to the endoscope. Preferably, the reinsertion tool has an outside diameter greater than the inside diameter of the lumen of the endoscope. Also preferably, the lumen of the reinsertion tool has an inside diameter sized to accommodate the catheter, but less than the inside diameter of the lumen of the endoscope. The reinsertion tool may further include a keel sized to fit in the channel of the catheter.

BRIEF DESCRIPTION OF THE DRAWINGS

FIG. 1 is a perspective view of a catheter in accordance with the present invention, having a U-shaped channel and guide wire lumen for directing a guide wire along its shaft and for facilitating rapid catheter exchange;

FIG. 1C is an enlarged fragmentary perspective view of the catheter of FIG. 1 at circle C;

FIG. 3 is a perspective view of an endoscope exchange sheath assembly, without slit, suitable for receiving the catheter of FIG. 1;

FIG. 3A is an enlarged fragmentary perspective view of the encircled sheath section of FIG. 3 at 3A;

FIG. 4 is a perspective view of an alternative embodiment sheath assembly having a slit sheath and two-piece hub, shown in an unlocked position;

FIG. 4A is a perspective view of the two-piece hub of FIG. 4 in a locked position;

FIG. 4B is an enlarged fragmentary perspective view of the encircled sheath section of FIG. 4 at 4B, having a slit;

FIG. 4C is an enlarged fragmentary perspective view of a sheath section, having an overlap, an alternate embodiment of the sheath in FIG. 4B;

FIG. 5 is a perspective view of the catheter of FIG. 1 inserted through the endoscope sheath assembly of FIG. 4;

FIG. 7A is a perspective view of the sheath assembly of FIG. 7, having the catheter removed;

FIG. 9A is an enlarged, cross-sectional view of an alternative embodiment of the introducer of FIG. 8;

FIG. 9B is an enlarged, cross-sectional view of another alternative embodiment of the introducer of FIG. 8;

FIG. 9C is an enlarged, cross-sectional view of another alternative embodiment of the introducer of FIG. 8;

FIG. 9D is an enlarged, cross-sectional view of another alternative embodiment of the introducer of FIG. 8;

FIG. 9E is an enlarged, perspective view of another alternative embodiment of the introducer of FIG. 8;

FIG. 9F is an enlarged, cross-sectional view of another alternative embodiment of the introducer of FIG. 8;

FIG. 10 is a perspective view of an illustrative locking device;

FIG. 14 is a perspective view of yet another illustrative locking device;

FIG. 15 is a partial side view of another illustrative locking device positioned on an endoscope having an angled side port;

FIGS. 18A, 18B, and 18C are enlarged views of an insertion tool in accordance with a second embodiment of the present invention;

FIG. 19 is a perspective view of a re-insertion tool in accordance with a first embodiment of the present invention;

FIGS. 20A–20F are isometric, top, left side, right side, rear and front views, respectively, of the re-insertion tool illustrated in FIG. 19;

FIG. 20G is a cross-sectional view taken along line 20G—20G in FIG. 20F;

DETAILED DESCRIPTION OF THE INVENTION

Figure 1B:
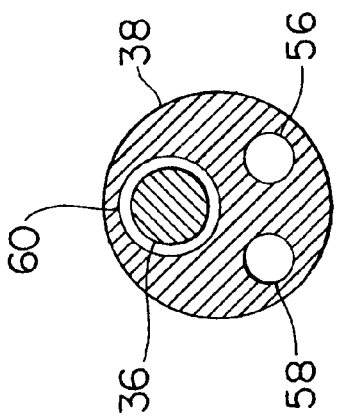
FIG. 1B is a cross-sectional view of the catheter with guide wire of FIG. 1 taken along the line B—B.

The following detailed description should be read with reference to the drawings in which similar elements in different drawings are numbered the same. The drawings, which are not necessarily to scale, depict selected preferred embodiments and are not intended to limit the scope or spirit of the invention.

FIG. 1 shows a perspective view of a catheter assembly 30 in accordance with the present invention. Catheter assembly 30 is used in catheter procedures for accessing targeted anatomical regions through the alimentary canal. The present invention incorporates features which allow rapid exchange of a catheter by a single operator. The catheter of the present invention allows shorter length guide wires to be used, resulting in procedures which require less medical personnel, are less time consuming, and less costly. Additionally, the present invention is adaptable to most catheter devices used for catheter procedures within the alimentary canal.

Catheter assembly 30 includes a catheter hub assembly 32 and a catheter 34, having a guide wire 36 passing through a portion thereof. Catheter 34 includes a shaft 38, which in general terms has a proximal end 40, a U-channel 42, a distal tip region 44, a distal end 46 and various lumens described in greater detail below. Catheter hub assembly 32 is operably connected to proximal end 40 of shaft 38. Catheter hub assembly 32 is preferably configured to couple to ancillary devices allowing access to a lumen within shaft 38.

Shaft 38 is a generally tubular shaped member having a generally uniform outer shape at proximal end 40. Shaft 38 may be sized for slidable passage through the lumen of an endoscope (not shown). Shaft 38 is preferably formed in an extrusion process. Shaft 38 may be formed of an extruded polymeric material. In one embodiment, the preferred polymeric material is polytetrafluoroethylene, polyether block amide, nylon or a combination or blend of these. Catheters which are contemplated include, but are not limited to, cannulas, sphincterotomes, cytology devices, and devices for stone retrieval and stent placement.

In a preferred embodiment, shaft 38 further includes a distal taper 48 which tapers to distal tip region 44. Additionally, tip region 44 may include high contrast, color coded distal markers 50. Finally, distal end 46 may be radiopaque for fluoroscopic visualization of distal tip region 44 during a catheter procedure.

U-channel 42 of shaft 38 extends between a first, proximal channel end 52 and a second, distal channel end 54. U-channel 42 serves to contain, but not necessarily constrain, guide wire 36, between channel proximal end 52 and channel distal end 54. The term "U-channel" refers to a channel shape that allows radial removal of guide wire 36 from the channel 42, and need not be strictly in the shape of the letter U. Channel 42 in the preferred embodiment is sufficiently large to allow unhindered radial guide wire 36 movement out of channel 42. Further, the channel walls and radial opening are substantially equal to or slightly larger than the diameter of a guide wire lumen, described in greater detail below. Although it is recognized that proximal channel end 52 may be located at any location distal of proximal end 40 of shaft 38, channel distal end 54 is preferably located between 10 and 40 cm from distal end 46 of catheter shaft 38.

Figure 1A:
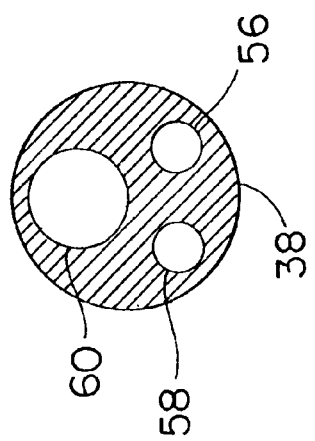
FIG. 1A is a cross-sectional view of the catheter of FIG. 1 taken along the line A—A.

Finally, as shown in FIG. 1A, which is a cross-sectional view of shaft 38 taken along line A—A at a location proximal of channel proximal end 52, shaft 38 includes ancillary lumen 56, ancillary lumen 58 and guide wire lumen 60.

Ancillary lumen 56 and ancillary lumen 58 extend longitudinally between proximal end 40 and distal end 46 of shaft 38. Ancillary lumen 56 and ancillary lumen 58 may be injection lumens, allowing for high contrast media flow capability for bubble-free opacification and for excellent visualization of a desired anatomical region. Additionally or alternatively, ancillary lumen 56 and/or ancillary lumen 58 may be used for or as part of other ancillary devices, such as a cutting wire lumen or a retrieval balloon lumen.

Guide wire lumen 60 extends longitudinally between proximal end 40 and distal end 46 of shaft 38 in the preferred embodiment. Further, guide wire lumen 60 is sized to receive guide wire 36. Guide wire lumen 60 may be a tubular member which is extruded integral catheter shaft 38, or alternatively, guide wire lumen 60 may be a separate tubular member which is coupled to catheter shaft 38. Although in one preferred embodiment the guide wire lumen 60 is a tubular member which is located proximate distal end 46 of catheter shaft 38, it is recognized that guide wire lumen 60 may be formed anywhere along shaft 38, may be an extension of shaft 38 coupled to distal end 46, or guide wire lumen 60 may run the entire length of shaft 38.

Referring to FIG. 1B, a cross-sectional view of shaft 38 taken along line B—B of FIG. 1 is shown. Guide wire 36 may access guide wire lumen 60 at a point proximal channel distal end 54. Guide wire 36 extends within channel 42 to channel distal end 54, continuing within guide wire lumen 60 through distal tip region 44, and exiting through an opening in distal end 46.

Referring to FIG. 1C, a section of catheter shaft 38 having U-channel 42 is shown. The embodiment shown also includes ancillary lumens 56 and 58. Sections of shaft 38 proximate the channel proximal end 52 and distal channel distal end 54 contain guide wire lumen 60 in communication with U-channel 42. In one embodiment, U-channel 42 has an interior, closed-side geometry, substantially the same as the geometry of guide wire lumen 60. Further, U-channel 42 walls are spaced further than a diameter of guide wire 36 such that guide wire 36 moves freely into and out of U-channel 42.

Catheter shaft 38 can be configured such that U-channel 42 is defined separately from guide wire lumen 60. With this approach, guide wire lumen 60 is divided into two sections; a first section extending between proximal end 40 of shaft 38 and channel proximal end 52; and a second portion extending between channel distal end 54 and distal end 46 of shaft 38. Alternatively, the shaft can be configured to define guide wire lumen 60 as extending longitudinally between proximal end 40 and distal end 46 of shaft 38. In the alternative embodiment, between channel proximal end 52 and channel distal end 54, guide wire lumen 60 is integral with U-channel 42. In other words, guide wire lumen 60 defines a portion of U-channel 42 such that spacing between outer walls of U-channel 42 is equal to a diameter of guide wire lumen 60. Regardless of how guide wire lumen 60 and U-channel 42 are defined, U-channel 42 provides for access to guide wire lumen 60 at channel distal end 54. In this regard, channel distal end 54 can be enlarged to more easily direct guide wire 36 into guide wire lumen 60.

Guide wire lumen 60 and U-channel 42 allow rapid exchange of catheter assembly 30 when an alternative catheter is necessary during a certain medical procedure. Shorter length guide wires may be used since guide wire 36 does not pass through shaft proximal end 40 and hub assembly 32, but rather exits the catheter shaft 38 at U-channel 42 located substantially distal from proximal end 40. The unique catheter construction in accordance with the present invention will reduce catheter therapeutic and diagnostic procedure time since catheter device exchanges may be performed relatively more easily and quickly by a single operator. Additional personnel and time associated with maintaining the placement of a conventional (approximately 400 cm) guide wire within the targeted anatomical region is eliminated, reducing the overall costs of the procedure.

Figure 1E:
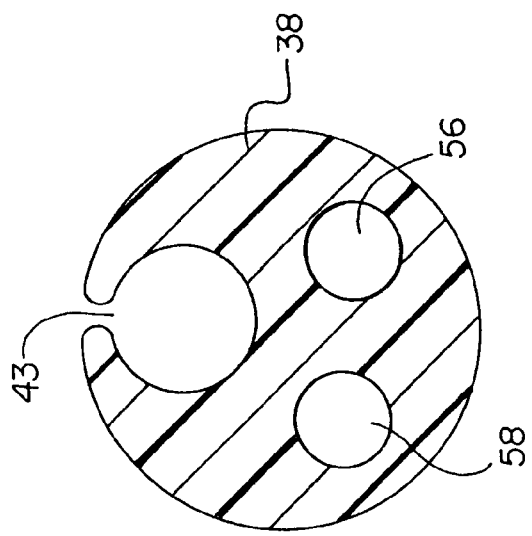
FIGS. 1D and 1E are cross-sectional views of the fragment illustrated in FIG. 1C.
Figure 1D:
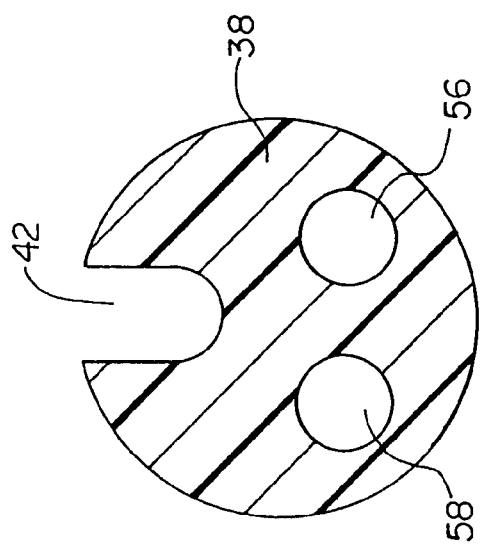

Referring now to FIGS. 1D and 1E, which are cross-sectional views of the shaft 38 fragment illustrated in FIG. 1C. Specifically, FIG. 1D is a precise cross-sectional view of the shaft 38 fragment illustrated in FIG. 1C, and FIG. 1E is an alternative cross-sectional view of the shaft 38 fragment illustrated in FIG. 1C. As described previously and now with reference to FIG. 1D, catheter shaft 38 includes a U-channel 42, a first ancillary lumen 56 and a second ancillary lumen 58. In this embodiment, U-channel 42 collectively defines a guide wire lumen and a slot providing access to the guide wire lumen. Similarly, in the embodiment illustrated in FIG. 1E, C-channel 43 collectively defines a guide wire lumen and a narrower slot for accessing the guide wire lumen. The narrower slot of C-channel 43 may have a dimension of approximately 0.018±0.002 inches and is designed to better contain the guide wire therein. C-channel 43 may eliminate the need for a separate exchange sheath when using endoscopes with larger lumens.

Figure 2A:
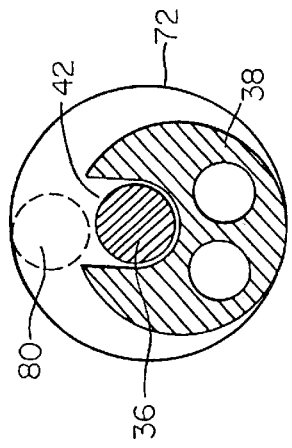
FIGS. 2A–2D are cross-sectional views of the catheter of FIG. 1 located within increasingly larger endoscope channels.

Referring to FIGS. 2A through 2D, cross-sectional views of endoscope working channels 70–76 containing a catheter according to FIG. 1 are shown. In the examples illustrated in FIGS. 2A through 2D, working channel inside diameters 70, 72, 74, and 76 are 2.8, 3.2, 3.8, and 4.2 mm, respectively. FIG. 2A illustrates catheter shaft 38 having ancillary lumens 54 and 56, U-channel 42, and guide wire 36 within U-channel 42. Further, shaft 38 is shown within a first size endoscope working channel 70. In FIG. 2A, guide wire 36 is effectively radially constrained by small sized working channel 70 that closely surrounds U-channel 42.

Figure 2B:
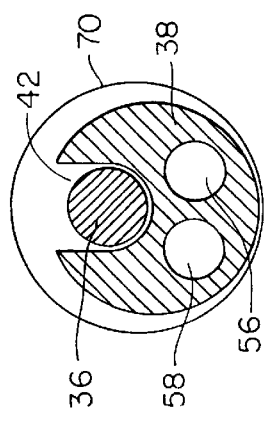
Figure 2D:
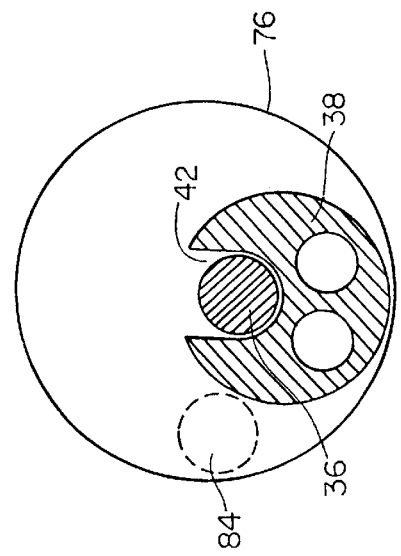
Figure 2C:
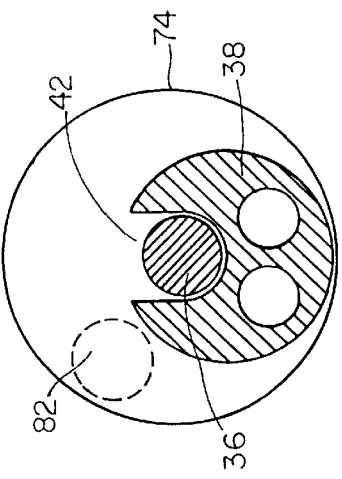

FIG. 2B illustrates catheter containment within a second size working channel 72, slightly larger than the working channel 70 of FIG. 2A. In FIG. 2B, guide wire 36 is able to move out of U-channel 42 to a position denoted with dashed lines at 80. FIG. 2C shows shaft 38 contained within a third, even larger sized working channel 74. Guide wire 36 is able to move completely out of U-channel 42 to position 82 shown with dashed lines. Finally, FIG. 2D demonstrates catheter shaft 38 within a fourth size working channel 76. In this even larger working channel, guide wire 36 lies within an even larger cross-sectional area, and is able to move to a position shown in FIG. 2D with dashed lines at 84.

As shown with the larger endoscope working channels (FIGS. 2C and 2D), the potential for guide wire 36 to slip out of U-channel 42 creates a potential for the guide wire 36 to become pinched and restrict desired movements of both guide wire 36 and catheter shaft 38. For this reason, when larger endoscope working channels are used, an exchange sheath having a sufficiently small inner diameter so as to constrain guide wire movement to within the catheter U-channel 42 is employed with the preferred embodiment. Generally speaking, an endoscope exchange sheath in accordance with the preferred embodiment allows for use of a radially accessible guide wire, which is longitudinally aligned with the catheter, while presenting a circular profile to an endoscope and mitigating guide wire pinching problems between the catheter and the endoscope working channel wall.

Referring to FIG. 3, an endoscope exchange sheath assembly 100 having sheath hub assembly 102 and a sheath 104 is shown. The sheath 104 includes a lumen 106 and a distal end 108. FIG. 3A shows a section of sheath 104, having lumen 106 for receiving a catheter. Basically, with reference to FIG. 1, catheter 34 is fed through lumen 106 of sheath 104 such that sheath 104 encompasses guide wire 36 within U-channel 42. Sheath 104 is adapted to be disposed within an endoscope working channel, thereby providing a smaller diameter channel than that of the surrounding endoscope working channel constraining the guide wire 34 (FIG. 1) to the U-channel 50 (FIG. 1), and mitigating the potential problems shown in FIGS. 2C and 2D.

Referring to FIG. 4, an alternate endoscope exchange sheath assembly 110 is shown. Sheath assembly 110 includes a two-piece hub assembly 112 and a sheath 114 defining lumen 116 and having slit 118 extending longitudinally over its length, terminating at distal end 120. Slit 118 in sheath 114 is shown in more detail in FIG. 4B.

Referring again to FIG. 4, two-piece hub assembly 112 has a proximal hub portion 122 and a distal hub portion 124, having a proximal slit 126 and a distal slit 128, respectively. Sheath slit 118 is in communication with hub slits 126 and 128, allowing a guide wire (not shown) to be radially slid into or out of sheath assembly 110. Proximal hub portion 122 is shown unlocked (position "A") in FIG. 4, aligning hub proximal slit 126 with hub distal slit 128 and sheath slit 118, providing a continuous slit for guide wire radial movement into and out of the sheath assembly 110. Proximal hub portion 122 is shown locked, in position "B", in FIG. 4A, whereby proximal hub slit 126 is rotated with respect to distal hub slit 128, preventing a guide wire (not shown) within hub assembly 112 from being moved radially out of hub assembly 112. Proximal hub portion 122 is set to position B (FIG. 4A) when radial guide wire movement is not desired.

FIG. 4C illustrates a portion of an alternate embodiment sheath 130 having a lumen 132, a sheath wall opening 134 and sheath wall overlap 136. A guide wire (not shown) is able to be slid out of lumen 132 of sheath 130 by maneuvering the guide wire into sheath wall opening 134 and through overlap 136.

Referring to FIG. 5, catheter assembly 30 depicted in FIG. 1 is shown inserted within endoscope exchange sheath assembly 110 depicted in FIG. 4. More particularly, catheter 34 is inserted through slitted sheath assembly 110, extending distally out sheath distal end 120. Guide wire 36 (shown partially in FIG. 5) is positioned within U-channel 42 of catheter 34, along guide wire lumen 60 (FIG. 1B), and extends from shaft distal end 46. Further, guide wire 36 is engaged by hub assembly 112. More particularly, guide wire 36 passes within and is engaged by proximal slit 126 and distal slit 128 of hub assembly 112. Sheath proximal hub portion 122, having proximal slit 126, is shown in locked position relative to sheath distal hub portion 124, having distal slit 128. Thus, in the locked position, hub assembly 112 of sheath assembly 110 prevents radial withdrawal of guide wire 36, otherwise inserted in U-channel 42 of catheter 34, from distal the channel proximal end 52.

Figure 6:
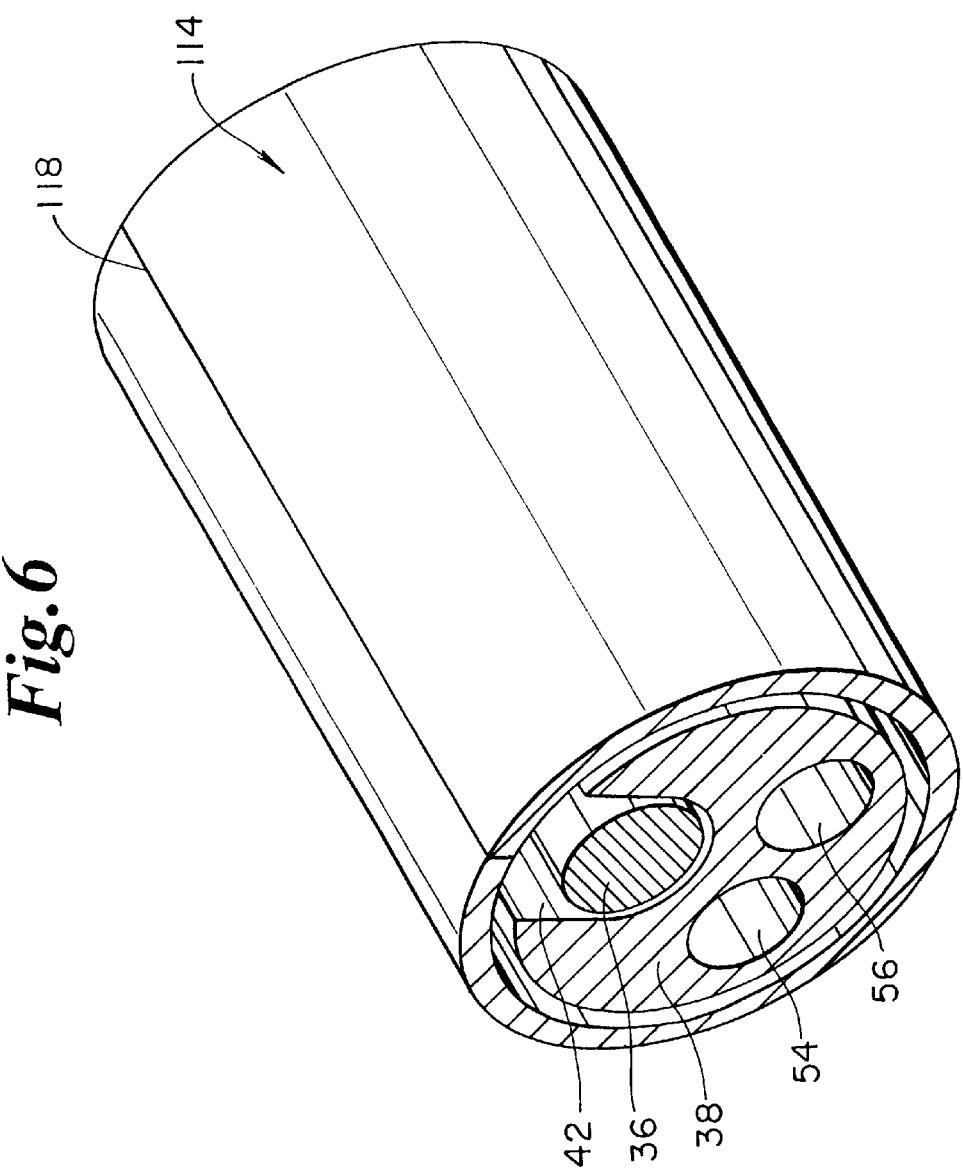
FIG. 6 is a perspective view of an endoscope sheath section containing a catheter having a U-shaped channel containing a guide wire.

Referring to FIG. 6, a section of FIG. 5 is shown in detail, having endoscope sheath 114 containing catheter shaft 38, which further maintains guide wire 36 within U-channel 42. As shown, sheath 114 is able to constrain movement of guide wire 36 from U-channel 42 when sheath 114 is within a larger endoscope working channel, for example as illustrated in FIGS. 2C and 2D. Importantly, the sheath 114 embodiment illustrated in FIG. 6 includes longitudinal slit 118, allowing guide wire 36 to be peeled from catheter shaft 38 and endoscope sheath 114. In other words, as previously described, U-channel 42 is sized larger than guide wire 36 such that guide wire 36 can displace radially from U-channel 42. Sheath 114 prevents undesired displacement of guide wire 36 from U-channel 42 under normal operating conditions. However, if adequate radial force is placed on guide wire 36 by an operator, guide wire 36 will separate sheath 114 along slit 118 such that guide wire 36 is displaced from sheath 114 and U-channel 42.

Figure 7:
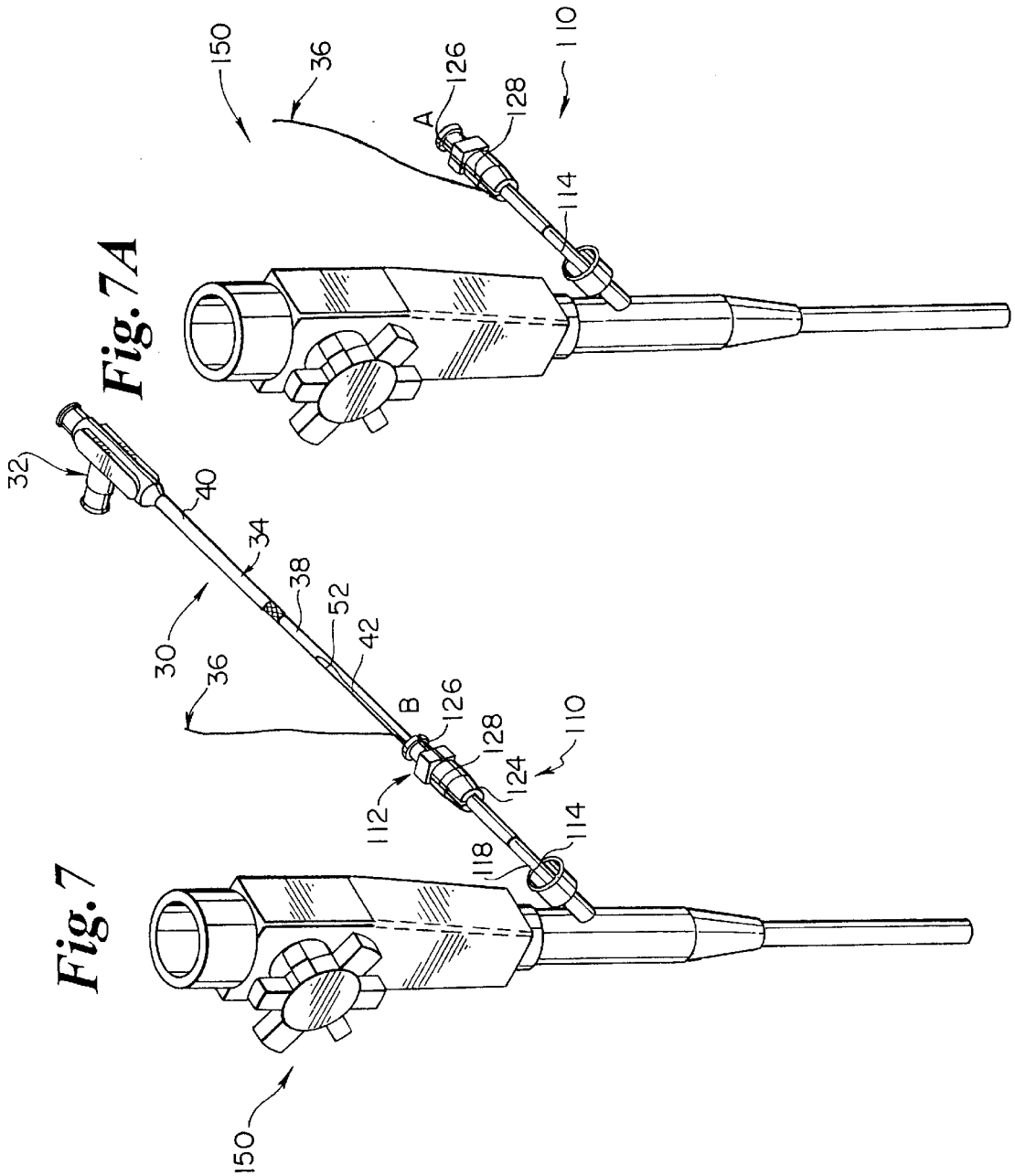
FIG. 7 is a partial perspective view of a guide wire within the catheter of FIG. 1 inserted through the endoscope sheath assembly of FIG. 4, which is in turn within an endoscope.

Referring to FIG. 7, guide wire 36 is shown inserted within catheter assembly 30 of FIG. 1, which is inserted through endoscope sheath assembly 110 of FIG. 4, which is in turn within an endoscope 150. Sheath assembly 110 includes sheath 114 that has slit 118 and two-piece hub assembly 112, shown at a locked position "B" (also in FIG. 4A). Having hub assembly 112 locked prevents guide wire 36 from moving radially out of sheath 114 through slit 118. Guide wire 36 can be restrained from longitudinal movement by applying finger pressure on the guide wire 36 against hub assembly 112.

Referring to FIG. 7A, endoscope 150 and sheath assembly 110 of FIG. 7 are shown without the catheter assembly 30 inserted, as after catheter withdrawal. Sheath hub assembly 112 is shown in unlocked position at "A" (also in FIG. 4). Having hub assembly 112 unlocked allows radial movement of guide wire 36 out of sheath 114 through slit 118, but such movement may be restrained by trapping guide wire 36 against the outside of sheath 114 using one finger, providing ease of guide wire 36 control during catheter exchanges.

In one possible endoscopic procedure, an endoscope 150, as illustrated in FIG. 7, is first introduced into the mouth of a patient and is guided through the patient's alimentary canal. Specifically, endoscope 150 is guided down the esophagus, through the stomach, past the pyloric sphincter of the stomach and into the duodenum. Endoscope 150 has a lumen extending longitudinally between its proximal end and the distal end.

Endoscope 150 is guided through the alimentary canal until a distal end (not shown) of endoscope 150 is proximate the target area within the anatomy to receive treatment. In an endoscopic biliary procedure, endoscope 150 is guided into the duodenum until the opening at the distal end of the endoscope 150 is proximate the papilla of vater. The papilla of vater is located between the sphincter of oddi, which leads to the common bile duct, hepatic, and pancreatic ducts. The proximal end (shown in FIGS. 7 and 7A) of endoscope 150 extends and remains outside the mouth of the patient.

With endoscope 150 properly positioned within the patient, catheter assembly 30 is prepared for insertion into the endoscope. First, guide wire 36 is fed into the guide wire lumen 60 (FIGS. 1A–1C) of shaft 38. More particularly, a distal end of guide wire 36 is placed within U-channel 42, distal the channel proximal end 52. The guide wire 36 is then fed to channel distal end 54 (FIG. 1) into guide wire lumen 60. Finally, guide wire 36 is fed through shaft 38 to distal tip region 40 (FIG. 1). In one method, catheter 32 is then inserted directly into endoscope 150 working channel. This method may be practiced with an endoscope having a sufficiently small working channel inside diameter, as illustrated in FIG. 2A, to constrain guide wire 36 movement without a sheath.

However, in a preferred method (with reference to FIG. 7), catheter assembly 30, threaded with guide wire 36, is inserted into sheath assembly 10, thereby constraining guide wire 36 from slipping radially out of U-channel 42. More particularly, catheter 34 is inserted into endoscope 150 working channel, but leaving channel proximal end 52 proximate sheath hub assembly 112, and leaving a portion of guide wire 36 extending from the channel proximal end 52 as well. Notably, sheath hub assembly 112 includes hub slits 126 and 128 which receive a portion of guide wire 36. Thus, in the preferred embodiment, hub assembly 112 is locked, preventing unwanted radial guide wire 36 movement. In a preferred method, the loading of guide wire 34 into catheter shaft 38 and catheter shaft 38 into sheath assembly 110 is done prior to inserting endoscope 150 into a patient (not shown).

Endoscope sheath 114, containing catheter shaft 38, is inserted into endoscope 150 working channel. Endoscope sheath 114 serves to constrain radial guide wire 36 movement over the approximate length of U-channel 42. Catheter shaft 38 and sheath 114 are inserted together into endoscope 150 until both are near a distal end (not shown) of endoscope 150. Catheter shaft 38 and sheath 114 may be, either or both, advanced until exiting the distal end of endoscope 150.

In one method, guide wire 36 is advanced until guide wire 36 distal tip is positioned within the target area in the biliary tree (including the common bile, hepatic or pancreatic ducts). For example, the distal tip of guide wire 36 may be guided through the orifice leading to the papilla of vater for access to the biliary tree. Catheter shaft 38 may then be advanced over guide wire 36, tracking catheter assembly 30, until catheter distal tip region 40 (FIG. 1) exits distal end of endoscope 150 and is positioned within the desired duct. In another method, guide wire 36 and catheter assembly 30 are advanced together until catheter distal end 42 (FIG. 1) is positioned at the target area. It is also recognized that the catheter could be first advanced to near the target area, followed by inserting the guide wire when needed to advance the catheter further.

Once guide wire 36 is in position at the target area, catheter procedures, including injecting contrast media, such as radiopaque dye, through ancillary lumens 56 or 58 (FIG. 1A–1C) into the common bile duct for visualization of the duct, can be performed. After the desired catheter procedure has been completed, catheter assembly 30 can be exchanged or removed from endoscope 150, leaving guide wire 36 in position for other catheter procedures. Catheter assembly 30 and sheath assembly 110 may also be removed together.

One method of withdrawing catheter 34 from endoscope 150 is possible using either a slitted/overlapped endoscope sheath 114 as depicted in FIGS. 4 through 4C, or a sheath 104 without a slit as depicted in FIGS. 3 through 3A. Using this method, best visualized with reference to FIG. 7, guide wire 36 is held to prevent longitudinal movement while catheter 34 is retracted within endoscope sheath 114 (or 104). Catheter 34 retraction leaving the guide wire 36 in position within the patient is enabled by U-channel 42 being radially open to guide wire 36 removal in catheter shaft 36. Once catheter retraction has brought channel distal end 54 (FIG. 1) to a point proximate sheath hub assembly 112, only a relatively short portion of guide wire 36, from channel distal end 54 to distal end 46 (FIG. 1) of catheter shaft 38, remains within catheter 34. A single operator can remove this remaining portion of guide wire 36 from catheter 34 by first slightly retracting catheter assembly 30 (while still holding guide wire 34 in place) out of sheath assembly 110 (or 100), such that a portion of guide wire 36 is accessible distal of catheter distal end 46. In other words, a small portion of guide wire 36 is accessible between distal end 46 of catheter 34 and distal hub portion 124 of sheath assembly 110. The accessible portion of guide wire 36 is then held by the operator, while withdrawing the remaining portion of catheter 34 completely over guide wire 36. In an alternative method, the distal end of the endoscope can include an elevator which could be utilized to lock the distal end of the guide wire in position while the catheter is removed.

Exchange of endoscope sheath assembly 110 may be desired, as when a stent (not shown) is to be advanced over guide wire 36, and the stent has a larger outside diameter than can be accommodated by the sheath 114. One method of exchanging an endoscope sheath assembly 110 may be used where sheath 114 is slitted as in FIG. 4B, or overlapped, as in sheath 130 in FIG. 4C. Referring to FIG. 7A, two-piece hub assembly 112 is turned to the unlocked position "A" (also shown in FIG. 4). Guide wire 36 is pulled radially away from sheath hub assembly 112 and through slit 118 in sheath 114. Guide wire 36 is then held, preferably against some portion of endoscope 150, to prevent guide wire 36 from being dislodged from position within the patient. Sheath 114 is retracted from endoscope 150, guide wire 36 being "peeled" away from sheath 114. Sheath retraction is continued until sheath 114 is completely outside of endoscope 150 and over guide wire 36. At this point, guide wire 36 is within endoscope 150 working channel, and stents, catheters, and endoscope sheaths may be advanced over guide wire 36.

Another method of exchanging both endoscope sheath assembly 110 and catheter assembly 30 may be used where the sheath 114 is slitted as in FIG. 4B, or overlapped, as in sheath 130 in FIG. 4C. Referring to FIG. 7 and 7A, two-piece hub assembly 112 is turned to the unlocked position "A" (FIG. 7A). Guide wire 36 is pulled radially away from U-channel 42 of catheter 34, from hub assembly 112 and through slit 118 in sheath 114. Guide wire 36 is then held, preferably against some portion of endoscope 150, to prevent guide wire 36 from being dislodged from position within the patient. Sheath 114 and catheter 34 are retracted from endoscope 150, with guide wire 36 being "peeled" away from sheath 114. Sheath assembly 110 and catheter assembly 30 retraction are continued until sheath 114 and catheter 34 are completely outside of endoscope 150 and over guide wire 36. At this point, guide wire 36 remains in a position within endoscope 150 and patient. A single operator can access a small portion of guide wire 36 between distal end 46 (FIG. 1) of catheter 34 to hold guide wire 36 in place while catheter assembly 30 is completely removed or disengaged from guide wire 36.

While sheath assembly 110 has been described as including a two-piece hub assembly 112 in conjunction with sheath 114, other assemblies may be used. For example, referring to FIG. 8, an alternate sheath assembly 160 is shown. Sheath assembly 160 includes an introducer 162, an attachment means 164 and a sheath 166. Similar to previous embodiments, sheath 166 defines a lumen (not shown) and includes a slit 168 extending longitudinally over its length, terminating at a distal end 170. Sheath 166 is generally identical to sheath 104 and sheath 114 previously described. Introducer 162 is attached to sheath 166 by attachment means 164 such that lumen (not shown) of sheath 166 is in fluid communication with an interior portion of introducer 162. In one preferred embodiment, attachment means 164 is a flexible membrane which seals sheath 166 to introducer 162. Alternatively, other forms of attachment, such as an adhesive or frictional engagement between introducer 162 and sheath 166 may also be useful.

Figure 8:
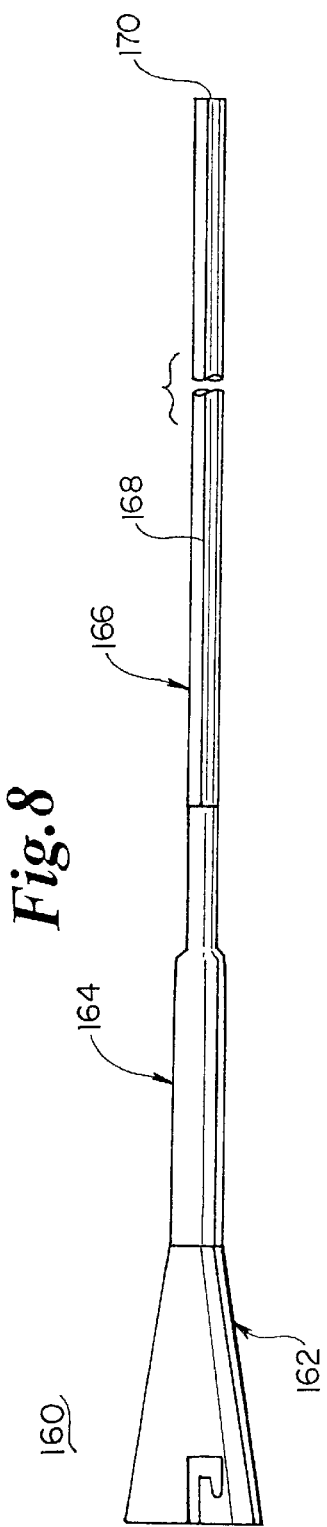
FIG. 8 is a partial perspective view of an alternative embodiment of a sheath assembly, including an introducer.
Figure 8A:
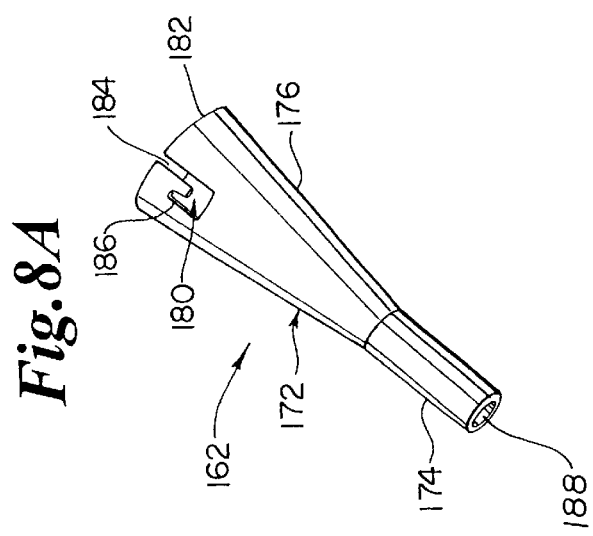
FIG. 8A is an enlarged perspective view of the introducer of FIG. 8.

Referring to FIG. 8A, introducer 162 is shown in greater detail. Introducer 162 is a funnel-shaped device including a horn 172 and a neck 174. In one preferred embodiment, horn 172 and neck 174 are integrally formed as a singular body.

Horn 172 is preferably a conically-shaped body having an outer wall 176. Outer wall 176 defines an interior space and includes a guide wire-receiving notch 180 formed near proximal end 182 of horn 172. Guide wire-receiving notch 180 is preferably J-shaped and includes an entry end 184 and a locking end 186. As shown in FIG. 8A, entry end 184 is open at proximal end 182 of horn 172. Conversely, locking end 186 is closed.

Neck 174 is preferably tubular in shape, and includes a passage 188. Passage 188 is configured to be in fluid communication with interior space of horn 172. In the preferred embodiment, horn 172 and neck 174 are formed of a plastic material. Alternatively, any other semi-rigid or rigid, surgically-safe material may be used.

Referring to FIGS. 1, 8 and 8A, during use, catheter assembly 34 (FIG. 1) is inserted within sheath assembly 160. More particularly, distal end 46 (FIG. 1) of catheter shaft 38 (FIG. 1), including guide wire 36 (FIG. 1) is placed within horn 172 of introducer 162. The conical shape of horn 172 assists in directing distal end 46 of catheter shaft 38, including guide wire 36, into passage 188 of neck 174. Catheter shaft 38 continues forward within lumen (not shown) of sheath 166 until distal end 46 of catheter shaft 38 extends from distal end 170 of sheath 166.

Once properly inserted within sheath assembly 160, a proximal end of guide wire 36 (FIG. 1) is maintained within guide wire-receiving notch 180. More particularly, a portion of guide wire 36 is forced by an operator through entry end 184 of guide wire-receiving notch 180 and forced within locking end 186 thereof. In this regard, locking end 186 preferably has a diameter slightly smaller than that of guide wire 36. Thus, locking end 186 frictionally maintains guide wire 36. Conversely, guide wire 36 can easily be released from guide wire-receiving notch 180 by sliding guide wire 36 from locking end 186 and out of entry end 184. Thus, sheath assembly 160 functions in a manner highly similar to sheath assembly 100 and sheath assembly 110 previously described.

Referring to FIG. 9A, an alternative embodiment of an introducer 190 is shown. Introducer 190 includes a horn 192, a neck 194 and a valve 196. Similar to previous embodiment, horn 192 and neck 194 are preferably integrally formed as a singular body. Horn 192 includes an outer wall 197 which defines a guide wire-receiving notch 198 and valve-receiving slots 200. Valve 196 includes a valve body 202 sized to fit within outer wall 197 of horn 192. Further, valve 196 includes ribs 204 extending from valve body 202. Ribs 204 are preferably sized to mate within valve-receiving slots 200 of horn 192. Thus, valve 196 is maintained within horn 192 via interaction of ribs 204 with valve-receiving slots 200. In this regard, valve-receiving slots 200 are preferably positioned along horn 192 proximal neck 194. Valve 196 is preferably made of a rubber-type material.

During use, introducer 190 functions in a manner highly similar to introducer 162 (FIGS. 8 and 8A) previously described. Additionally, however, valve 196 forms a seal about catheter shaft 38 (FIG. 1). Thus, upon insertion into a human body, valve 196 prevents bodily fluids, such as bile, from backing up through the sheath assembly. Additionally, valve 196 can provide for aspiration, if desired.

Referring to FIG. 9B, an alternative embodiment of an introducer 206 is shown. Introducer 206 is highly similar to introducer 190 (FIG. 9A) previously described. In this regard, introducer 206 includes a horn 208, a neck 210 and a valve 212. Horn 208 is preferably integrally formed with neck 210 and includes an outer wall 214 defining a guide wire-receiving notch 216 and valve-receiving slots 218. Similar to valve 196 (FIG. 9A), valve 212 includes a valve body 220 and ribs 222. Ribs 222 are sized to mate within valve-receiving slots 218 of horn 208. In this regard, valve-receiving slots 218 are positioned proximate a proximal end 224 of horn 208. Introducer 206, including valve 212, functions in a manner highly similar to introducer 190 (FIG. 9A) as previously described.

It is recognized that the fluid blocking function provided by valve 212 can be achieved with other designs. For example, referring to FIG. 9C, an alternative embodiment of an introducer 226 is shown. Introducer 226 includes a horn 228, a neck 230 and an O-ring 232. Horn 228 and neck 230 are preferably formed as an integral body. Horn 228 preferably includes a guide wire-receiving notch (not shown) similar to that previously described and an interior slot 234. Interior slot 234 is preferably positioned proximate neck 230 and is sized to maintain O-ring 232. Alternatively, interior slot 234 can be formed in neck 230.

O-ring 232 is preferably made of a rubber-type material. Further, O-ring 232 has an inner diameter slightly smaller than that of horn 228 and neck 230. Thus, during use, O-ring 232 forms a seal about catheter shaft 38 (FIG. 1), blocking passage of bodily fluids, such as bile, into horn 228.

Referring to FIG. 9D, another alternative embodiment of an introducer 236 is shown. Introducer 236 is similar to a touhey-borst system and includes an upper horn section 238, a lower horn section 240 and a grommet 242. Upper horn section 238 includes an outer wall 244 defining a proximal end 246, a grommet-receiving flange 248 and a distal end 250. Proximal end 246 of horn section 238 preferably includes a guide wire-receiving notch (not shown) similar to that previously described. Distal end 250 is threaded and includes a passage 252 sized to receive a portion of lower horn section 240.

Lower horn section 240 includes a body 254 defining a proximal end 256, an intermediate portion 258 and a distal end 260. An interior passage 266 is configured to communicate with passage 252 and extends from proximal end 256 to distal end 260. Finally, proximal end 256 includes a threaded slot 262 sized to threadably receive distal end 250 of upper horn section 238.

Grommet 242 is preferably made of a rubber-type material and is sized to nest within grommet-receiving flange 248 of upper horn section 238 while abutting proximal end 256 of lower horn section 240.

Introducer 236 is assembled by placing grommet 242 within grommet-receiving flange 248 of upper horn section 238. Distal end 250 of upper horn section 238 is then threadably secured to proximal end 258 of lower horn section 240. As upper horn section 238 is threadably secured to lower horn section 240, proximal end 256 of lower horn section 240 compresses grommet 242 within grommet-receiving flange 248 of upper horn section 238. During use, introducer 236 functions in a manner highly similar to that previously described. In this regard, grommet 242 forms a seal about catheter shaft 38 (FIG. 1). Further, aspiration can be achieved, if desired, by loosening lower horn section 240 relative to upper horn section 238.

Referring to FIG. 9E, yet another alternative embodiment of an introducer 266 is shown. Introducer 266 includes a horn 268, a neck 270 and a valve 272. Preferably, horn 268, neck 270 and valve 272 are integrally formed as a singular body. In this regard, valve 272 is formed while molding horn 268 and neck 270 by imparting a controlled flash at distal end 274 of neck 270.

Introducer 266 performs in a manner highly similar to that previously described. Thus, valve 272 forms a seal about catheter shaft 38 (FIG. 1), thereby preventing back flow of bodily fluids, such as bile, into horn 268.

Referring to FIG. 9F, another alternative embodiment of an introducer 276 is shown. Introducer 276 includes a horn 278, a neck 280 and a valve 282. Horn 278 and neck 280 are preferably integrally formed as a singular body. In this regard, horn 278 and neck 280 are defined by an outer wall 284. Outer wall 284 forms a guide wire-receiving notch 286 and an exterior slot 288. Guide wire-receiving notch 286 is similar to that previously described. Exterior slot 288 is positioned along neck 280 and is sized to maintain a portion of valve 282. Alternatively, exterior slot 288 can be positioned along horn 278.

Valve 282 is preferably a rubber-type sock defined by an upper rib 290, a side wall 292 and a shoulder 294. Upper rib 290 is preferably sized to mount within exterior slot 288 of neck 280. Side wall 292 is preferably flexible so as to stretch along neck 280. Finally, shoulder 294 is preferably configured to abut a distal end 298 of neck 280. With this configuration, valve 282 is placed over distal end 298 of neck 280 such that shoulder 294 contacts distal end 298. Due to the preferred flexible characteristic of valve 282, side wall 292 is stretched until upper rib 290 nests within exterior slot 288 of neck 280.

During use, the catheter shaft 38 (FIG. 1) is placed through introducer 276 such that shoulder 294 of valve 282 forms a seal about catheter shaft 38. Thus, valve 282 prevents undesired back flow of bodily fluids, such as bile.

FIG. 10 is a perspective view of an illustrative locking device for use with an endoscope having a side instrument port. The illustrative locking device is generally shown at 320 and includes a body member 322. At one end, the body member 322 includes one or more hook members 324 for attaching the locking device to a shaft of an endoscope or the like (see FIG. 11). At the other end, the body member 322 includes a securing mechanism for securing a guide wire or catheter to the locking device.

Figure 13:
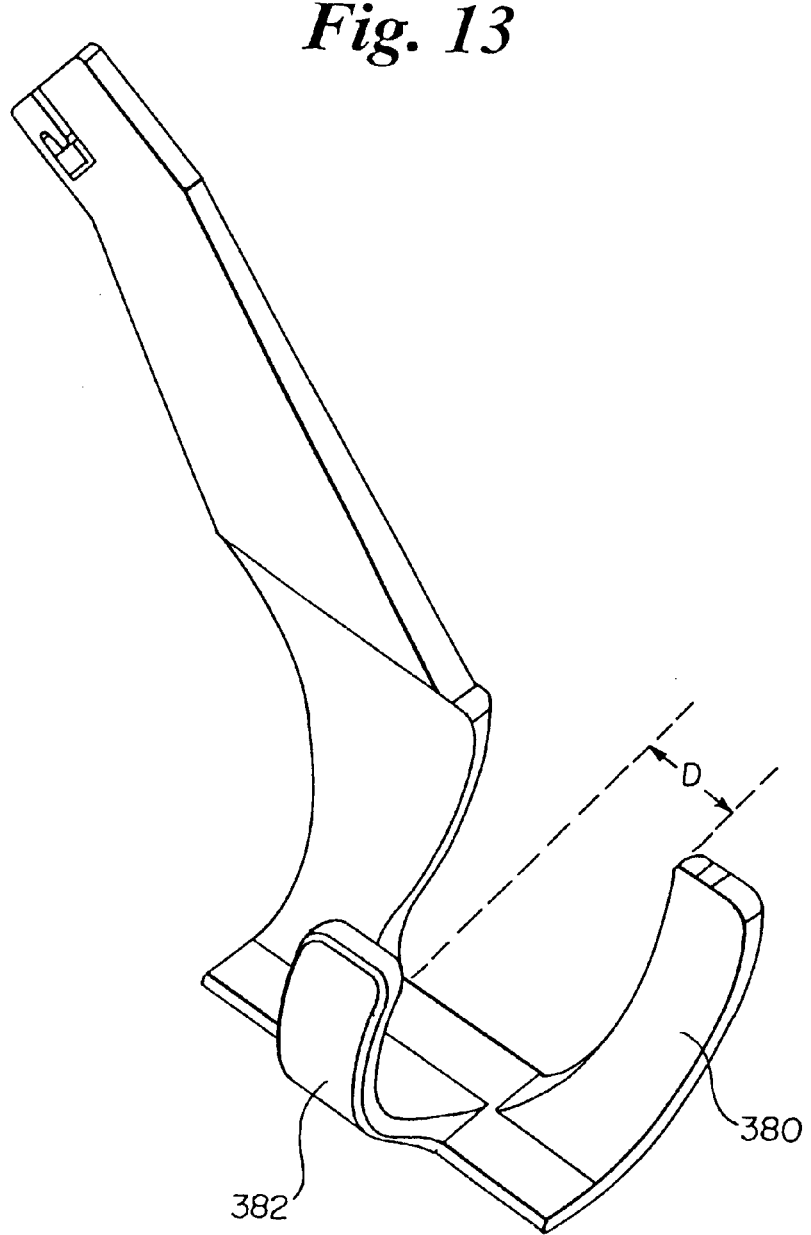
FIG. 13 is a perspective view of another illustrative locking device.

The hook members 324 may be provided in pairs, as shown in FIG. 10, or offset from one another, as shown in FIG. 13. In either case, the hook members 324 are adapted to clip and secure the locking device to the shaft of an endoscope or the like.

The securing mechanism preferably includes one or more openings provided in the body member 322. In the embodiment shown, the body member 322 includes a guide wire opening 326 and a catheter opening 332. The guide wire opening 326 is similar to the guide wire-receiving notch 180 of FIG. 8A. The guide wire opening 326 is preferably J-shaped, and preferably includes an entry slot 328 and a locking slot 330. The catheter opening 332 is boot shaped, and also preferably includes an entry slot 334 and a locking slot 336.

The entry slot 328 of the guide wire opening 326 is dimensioned to be larger than the diameter of a guide wire. The locking slot 330 of the guide wire opening 326 is dimensioned to be somewhat smaller than the diameter of a guide wire. Accordingly, a guide wire can be secured to the body member 322 by inserting a portion of the guide wire through the entry slot 328 of the guide wire opening 326 and into the locking slot 330. The locking slot 330 frictionally secures the guide wire relative to the body member 322.

Likewise, the entry slot 334 of the catheter opening 332 is dimensioned to be larger than the diameter of a catheter. The locking slot 336 of the catheter opening 332 is dimensioned to be somewhat smaller than the diameter of a catheter. Accordingly, a catheter can be secured to the body member 322 by inserting a portion of the catheter through the entry end 334 of the catheter opening 332 and into the locking slot 336. The locking slot 336 frictionally secures the catheter relative to the body member 322.

Figure 11:
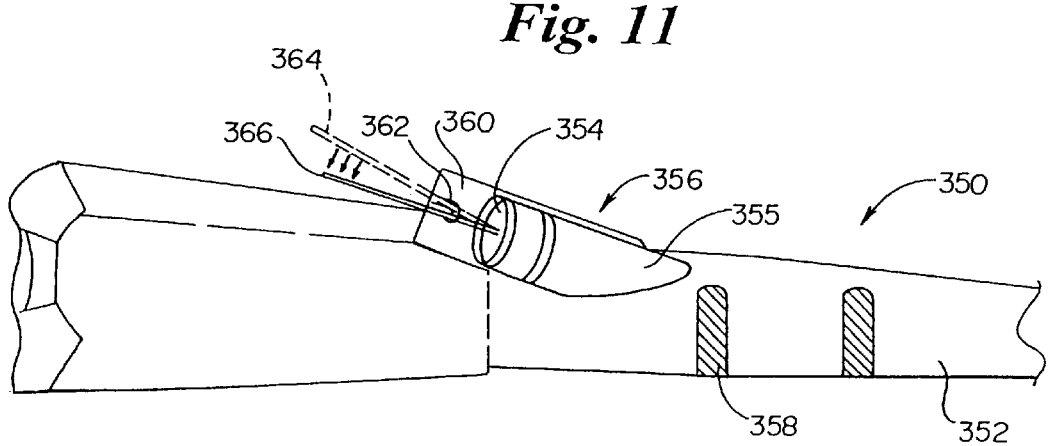
FIG. 11 is a partial side view of an illustrative locking device positioned on an endoscope having an angled side port.

FIG. 11 is a partial side view of an illustrative locking device positioned on an endoscope with an angled side port extending therefrom. The endoscope is generally shown at 350, and includes a main shaft 352 with a lumen extending therethrough. A side port 356 extends laterally away from the main shaft 352 at an angle. The side port 356 provides access to the lumen of the main shaft 352. Accordingly, a guide wire and/or catheter may access the lumen of the main shaft 352 via the side port 356.

The side port 356 preferably includes a side port opening 354 which is laterally spaced from the main shaft 352 due to the angular displacement between the main shaft 352 and the side port 356. The side port opening 354 is in fluid communication with the lumen of the main shaft 352 via a connection tube 355. The connection tube 355 intersects a side wall of the main shaft 352 at an angle, as shown.

A locking device having a body member 360 is shown clipped onto the main shaft 352 of the endoscope. The body member 360 includes a number of hook members 358 for attaching the locking device to the main shaft 352. Two hook members are visible in FIG. 11. The hook members 358 are similar to the hook members 324 described above with respect to FIG. 10.

The body member 360 extends away from the hook members 358 and generally parallel to the side port 356. In FIG. 11, the body member is obscured by the main shaft 352 and side port 356. The body member 360 extends upward past the side port opening 354, wherein a securing mechanism is provided. Preferably, the securing mechanism is a J-shaped guide wire opening 362.

In use, a guide wire is advanced into the body via the endoscope. During the advancement of the guide wire, the proximal end thereof may be moved to a first position 364, which is in the entry slot of the guide wire opening 362. Once the guide wire is in a desired position within the body, the guide wire may be moved to a second position 366, which is in the locking slot of the guide wire opening 362. The locking slot of the guide wire opening 362 frictionally secures the guide wire relative to the body member 360.

Figure 12:
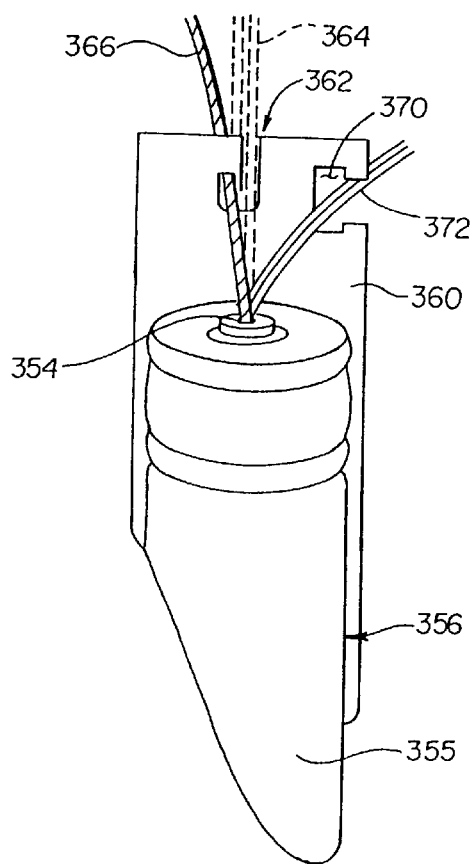
FIG. 12 is a partial side view detailing the illustrative locking device of FIG. 11.

FIG. 12 is a partial side view detailing the illustrative locking device of FIG. 11, with an additional oversized catheter opening shown. The side port of the endoscope is shown at 356, and the body member of the locking device is shown at 360. Positioned proximate the side port opening 354 is a guide wire opening 362 and an oversized catheter opening 370. Like above, the guide wire opening is J-shaped and includes an entry slot and a locking slot. Thus, the guide wire may be moved to the first position 364, which is in the entry slot of the guide wire opening 362. Once the guide wire is in a desired position within the body, the guide wire may be moved to the second position 366, which is in the locking slot of the guide wire opening 362. The locking slot of the guide wire opening 362 frictionally secures the guide wire relative to the body member 360.

The oversized catheter opening 370 is sized to restrict lateral movement of the catheter 372 but not longitudinal movement of the catheter 372. Providing a guide wire opening that can secure the guide wire relative to the body member, and an oversized catheter opening for only restricting lateral movement of the catheter 372 may be particularly useful in performing a catheter exchange procedure. For example, during a catheter exchange procedure, the guide wire opening may maintain the position of the guide wire. The oversized catheter opening 370 may separate the catheter from the guide wire, as the catheter is withdrawn. The first and second catheters should be single-operator exchange type catheters to provide access to the guide wire during the exchange.

FIG. 13 is a perspective view of another illustrative locking device. The embodiment shown in FIG. 13 is similar to the embodiment shown in FIG. 10, but the hook members are laterally offset rather than aligned. For example, hook member 380 is laterally offset from hook member 382 by a distance "D". This configuration is another example of an attachment mechanism for attaching the body member to a catheter shaft.

FIG. 14 is a perspective view of yet another illustrative locking device. The locking device is generally shown at 400, and includes a body member 401 having an attachment mechanism 402 at one end and a securing mechanism 404 at the other. The attachment mechanism 402 includes a first hook member 406 and a second hook member 408. The first hook member 406 and the second hook member 408 are adapted to extend around a substantial portion of the shaft of an endoscope or the like. Thus, the first hook member 406 and the second hook member 408 may clip the body member 401 to the desired shaft.

The securing mechanism 404 includes a J-shaped guide wire opening 410 and a flap-type catheter opening 412. The J-shaped guide wire opening 410 operates similar to that described above. The flap-type catheter opening 412 has a flap 414 formed by cutting the catheter opening 412 from the body member 401. The flap 414 is preferably curved to form a channel 416, wherein the end portion 418 of the channel 416 loops back to near the surface of the body member 401. In this configuration, a catheter or guide wire may be selectively provided in the channel 416, which may bend the flap away from the body member 401. Accordingly, the flap 412 may provide force between the guide wire or catheter and the body member 401 to effectively secure the guide wire or catheter to the body member 401.

FIG. 15 is a partial side view of yet another illustrative locking device 500. The locking device 500 is positioned between the side port 504 and the main shaft 506 of the endoscope 502. The locking device includes a body member 510 that is attached to the main shaft 506 using a strap 512. Preferably, the strap 512 extends around the entire circumference of the main shaft 506. Further, the body member 510 may include a guide wire opening 514 and one or more catheter openings 516, as shown.

Figure 16:
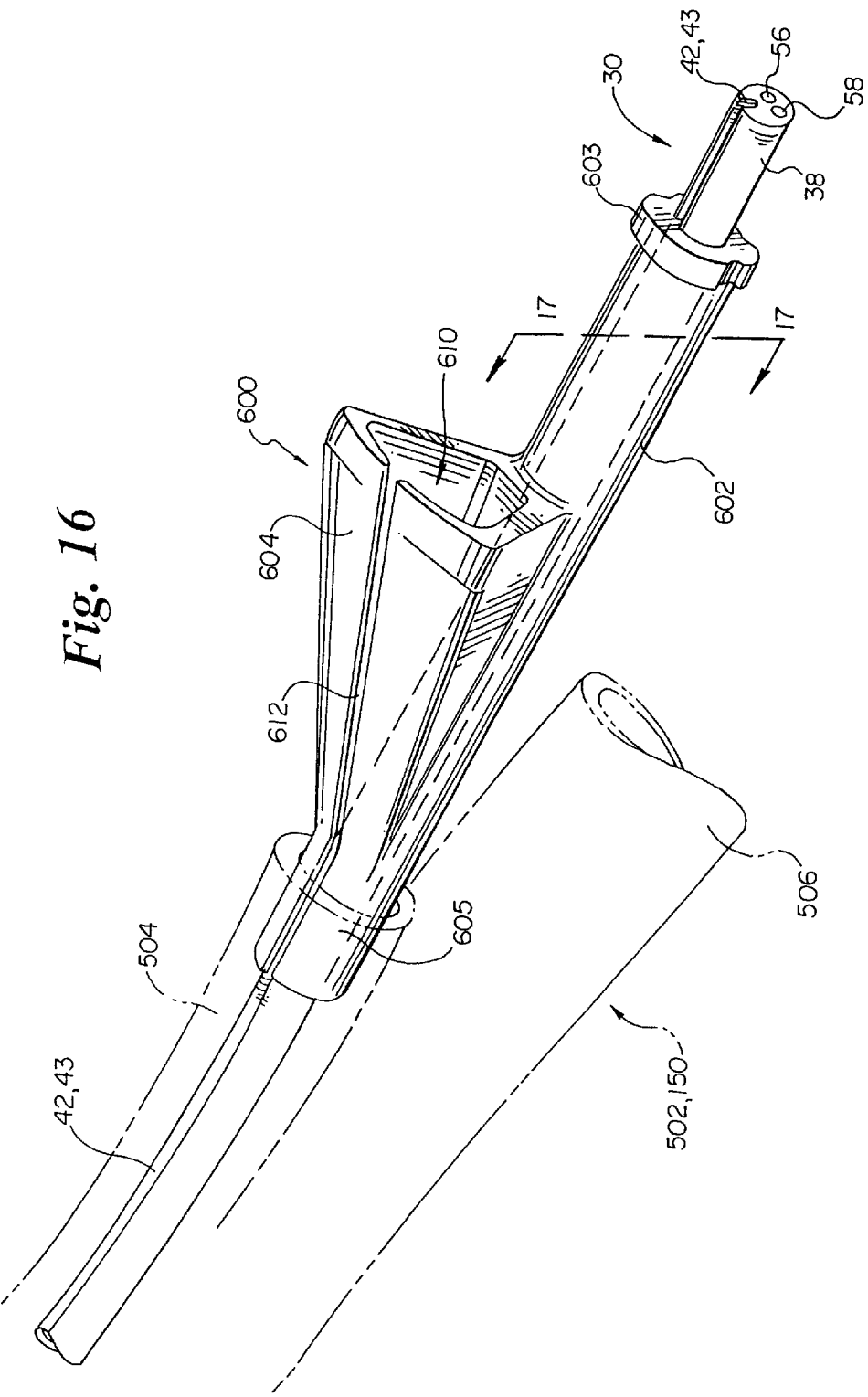
FIG. 16 is an enlarged fragmentary perspective view of an insertion tool in accordance with a first embodiment of the present invention.

Refer now to FIG. 16, which is an enlarged fragmentary perspective view of insertion tool 600 in accordance with an embodiment of the present invention. For purposes of clarity, only the shaft 38 of the catheter 30 has been illustrated. Similarly, only the side port 504 and the main shaft 506 of the endoscope 502/150 have been shown (in phantom). Except as described herein with specific reference to insertion tool 600, catheter 30 and endoscope 502/150 are the same as described previously. In addition, although not shown, it is to be understood that the insertion tool 600 and the catheter 30 are designed to be used in conjunction with a guide wire 36 as described previously.

As used herein, reference numerals 42 and 43 alternatively refer to U-channel 42 and C-channel 43, both of which include a slot and guide wire lumen therein. In some instances, reference numerals 42 and 43 may refer to the slot or guide wire lumen individually.

Insertion tool 600 includes a main body 602 and a funnel-shaped extension 604. The funnel-shaped extension 604 is connected to and disposed adjacent to the main body 602. The main body 602 includes a main lumen 606 extending therethrough. Main lumen 606 is sized to accommodate a shaft 38 of a catheter 30. Preferably, the insertion tool 600 is fixed or stationary at the proximal end of the catheter 30, but may also be slidably disposed thereon. For purposes of illustration only, the insertion tool 600 is shown in FIG. 16 as being slidable on the catheter 30.

Funnel-shaped extension 604 includes a funnel lumen 610 having a proximal opening and a distal, opening. The proximal opening of the funnel lumen 610 is significantly larger than the guide wire 36 designed for use in the catheter 30 such that the guide wire 36 may be easily inserted into the funnel lumen 610. The distal opening of the funnel lumen 610 is positioned and sized to communicate with the guide wire lumen 42/43 of the catheter 30 such that when the catheter 30 is disposed in the main lumen 606 of the main body 602, the guide wire may be easily inserted into the proximal opening of the funnel lumen 610 and into the guide wire lumen 42/43 of the catheter 30.

The distal portion of the main body 602 and the distal portion of the funnel-shaped extension 604 merge together to define a merged section 605 that has an exterior surface that is sized to fit within the lumen of the side port 504. A valve (not visible) is typically disposed in the lumen of the side port 504. The merged section 605 has sufficient length to engage and cross the valve disposed in the lumen of the side port 504. If the insertion tool 600 is slidably disposed on the catheter 30, unhindered longitudinal movement of the catheter 30 is permitted through the valve when the merged section 605 extends across the valve to maintain it in the open position. In addition, if a sheath is used, merged section 605 prevents the valve from damaging the thin-walled portion of the sheath.

The main lumen 606 and the funnel lumen 610 also merge together into a merged lumen (not visible) in the merged section 605. The distal opening of the funnel lumen 610 adjacent the merged lumen is aligned with the guide wire lumen 42/43 and is similarly dimensioned such that the guide wire passing through the merged lumen smoothly enters the guide wire lumen 42/43.

Main body 602 includes a proximal ridge 603 that provides a gripping surface for the user to slide the insertion tool 600 along the shaft 38 of the catheter 30 or to otherwise manipulate the insertion tool 600.

Figure 17A:
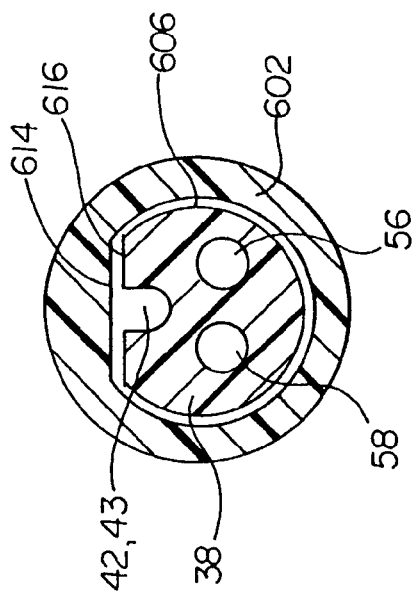
FIGS. 17A and 17B are cross-sectional views taken along line 17—17 in FIG. 16.

As illustrated in FIG. 17A, a first embodiment of the main body 602 further includes a tongue or key 608 protruding from the interior wall of the main body 602 into the main lumen 606. The tongue or key 608 extends along at least a portion of the length of the main body 602 preferably from the proximal ridge portion 603 to a point proximal of the distal merged section 605. The tongue 608 is aligned with the slot 42/43 and is sized to slidingly fit within the slot 42/43. With this arrangement, the tongue 608 maintains proper rotational alignment between the insertion tool 600 and the catheter 30. Specifically, the tongue 608 maintains alignment between the distal opening of the funnel lumen 610 and the guide wire lumen 42/43 of the catheter 30 such that the guide wire is automatically aligned with the guide wire lumen 42/43 upon insertion into the proximal opening of the funnel lumen 610.

Figure 17B:
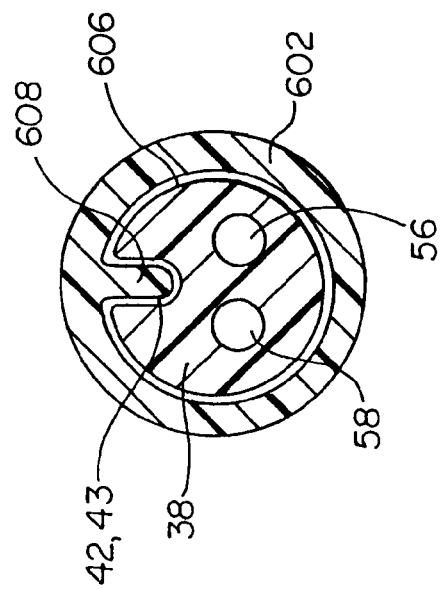

As illustrated in FIG. 17B, a second embodiment of the main body 602 further includes a non-round engaging surface 614 extending along the interior wall of the main body 602 into the main lumen 606. The non-round engaging surface 614 extends along at least a portion of the length of the main body 602, preferably from the proximal ridge portion 603 to a point proximal of the distal merged section 605. The non-round engaging surface 614 is aligned with a similarly shaped surface 616 extending along the side of the catheter 30. Both the engaging surface 614 of the insertion tool 600 and the engaging surface 616 of the catheter 30 are non-round (e.g., flat) to inhibit the rotation of the catheter 30 relative to the insertion tool 600. Thus, the engaging surfaces 614 and 616 maintain alignment between the distal opening of the funnel lumen 610 and the guide wire lumen 42/43 of the catheter 30 such that the guide wire is automatically aligned with the guide wire lumen 42/43 upon insertion into the proximal opening of the funnel lumen 610. Those skilled in the art will recognize that other non-round engaging surfaces 614, 616 may be utilized to prevent relative rotation between the catheter 30 and the insertion tool 600.

In preferred embodiments, funnel-shaped extension 604 also includes a slot or groove 612 providing access to the funnel lumen 610. The slot 612 extends along the length of the funnel-shaped extension 604 and the distal merged section 605. The slot 612 is sized to allow passage of a conventional guide wire 36 therethrough. The slot 612 permits the insertion tool 600 to be slid proximally along the shaft 38 of the catheter 30 without changing the position of the guide wire 36.

The insertion tool 600 may be made using conventional techniques such as injection molding and may be formed of any suitable medical grade polymer such as PP, ABS, or the like. The overall length of insertion tool 600 is approximately 1.50 inches, wherein the proximal portion of the main body 602 is approximately 0.50 inches in length, the funnel-shaped extension 604 is approximately 0.75 inches in length, and the distal merged section 605 is approximately 0.25 inches in length.

The inside diameter of the main body 602 is sized to accommodate catheter 30 and, therefore, may have an inside diameter of approximately 0.100 inches and an outside diameter of approximately 0.175 inches. Tongue 608 may have a width of approximately 0.0250 inches and a height of approximately 0.040 inches to correspond to the size and shape of the channel 42/43.

The funnel-shaped extension 604 may have a proximal outside profile of approximately 0.40 inches and a distal outside profile of approximately 0.185 inches providing a smooth transition to the distal merged section 605.

Merged distal section 605 may have an outside diameter of approximately 0.175 inches to snugly fit inside the lumen of the side port 504 and a length of approximately 0.250 inches to engage and cross the valve (not shown) in the side port 504.

The proximal opening of the funnel lumen 610 is significantly larger than the guide wire 36 to permit easy insertion of the guide wire 36 therein. The proximal opening of the funnel lumen 610 may have virtually any cross-sectional geometry that is significantly larger than the guide wire 36. For example, the proximal opening of the funnel lumen 610 may be a polygon having an average height of 0.20 inches and an average width of 0.20 inches.

In use, the insertion tool 600 may be placed on the catheter 30 such that the shaft 38 extends through the main lumen 606 of the main body 602. As mentioned previously, preferably the insertion tool 600 is fixed at the proximal end of the catheter 30, but may also be slidably disposed thereon. With the shaft 38 of the catheter 30 extending through the main lumen 606 and the tongue 608 extending into the slot 42/43 or the non-round surfaces 614, 616 engaging each other, the funnel lumen 610 is aligned with the guide wire lumen 42/43 of the catheter 30. The guide wire 36 may then be inserted into the proximal opening of the funnel lumen 610, through the distal opening of the funnel lumen 610, through the merged lumen of the distal merged section 605, and into the guide wire lumen 42/43 of the catheter 30.

If the insertion tool 600 is slidably disposed on the catheter 30, prior to inserting the guide wire, the insertion tool 600 may be advanced along the shaft 38 of the catheter 30 until the merged section 605 passes into the lumen of the side port 504 and across the valve disposed therein. When the merged section 605 is inserted into the lumen of the side port 504 a sufficient distance to open the valve disposed therein, the catheter 30 may be longitudinally moved without interference from the valve.

In addition, if the insertion tool 600 is slidably disposed on the catheter 30, after the guide wire 36 has been inserted into the guide wire lumen 42/43 of the catheter 30, the insertion tool 600 may be slid proximally along the shaft 38 while permitting the guide wire 36 to exit the funnel lumen 610 through the slot 612. In this manner, the guide wire 36 remains disposed in the guide wire lumen 42/43 of the catheter 30 while the insertion tool 600 is removed from the side port 504. This permits free manipulation of the catheter 30 and the guide wire 36 relative to the endoscope 502/150.

The above-described method of inserting the guide wire 36 into the guide wire lumen 42/43 of the catheter 30 utilizing the insertion tool 600 may be performed alone or in conjunction with other procedures described herein. For example, the insertion tool 600 may be used in procedures utilizing a sheath, lock mechanism, etc., as described herein.

Refer now to FIGS. 18A, 18B, and 18C, which illustrate enlarged views of an insertion tool 700 in accordance with an alternative embodiment of the present invention. FIG. 18A is a side view, FIG. 18B is an end view and FIG. 18C is a top view of insertion tool 700. Except as described herein, insertion tool 700 is the same in form and function as insertion tool 600 described with reference to FIGS. 16–17. A notable difference is that the insertion tool 700 is preferably movable on the catheter 30, but may also be fixed thereon.

Insertion tool 700 includes a main body portion 702 and a funnel-shaped extension 704. The main body 702 and the funnel-shaped extension 704 include a main lumen 706 extending therethrough. Main lumen 706 is sized to accommodate a shaft 38 of a catheter 30 (not shown). Preferably, the insertion tool 700 is slidably disposed on the catheter 30, but may also be fixed or stationary at the proximal end thereof.

Funnel-shaped extension 704 also includes a funnel lumen 710 having a top opening 714 tapering to a bottom opening 716 which provides access to the main lumen 706. The top opening 714 of the funnel lumen 710 is significantly larger than the guide wire 36 (not shown) designed for use in the catheter 30 such that the guide wire 36 may be easily inserted into the funnel lumen 710. The bottom opening 716 of the funnel lumen 710 is positioned and sized to communicate with the guide wire lumen 42/43 of the catheter 30 such that when the catheter 30 is disposed in the main lumen 706, the guide wire 36 may be easily inserted into the top opening 714 of the funnel lumen 710 and into the guide wire lumen 42/43 of the catheter 30.

The main body 702 has sufficient length to engage and cross the valve disposed in the lumen of the side port of the endoscope 502/150 (not shown). The main body 702, when inserted into the side port of the endoscope 502/150, extends across the valve such that the valve is maintained in the open position. If the insertion tool 700 is slidably disposed on the catheter 30, unhindered longitudinal movement of the catheter 30 is permitted through the valve when the main body 702 extends across the valve to maintain it in the open position. In addition, if a sheath is used, the main body 702 prevents the valve from damaging the thin-walled portion of the sheath.

As best seen in FIG. 18B, the funnel-shaped portion 704 further includes a tongue or key 708 protruding from the interior wall defining the main lumen 706. The tongue or key 708 extends along at least a portion of the length of the funnel shaped extension 704, and preferably along the length of the bridge portion 720 as best seen in FIG. 18C. The tongue or key 708 is sized to snugly fit within the slot 42/43 of the catheter 30 and is aligned with the slot 42/43 when the insertion tool 700 is disposed on the catheter 30.

With this arrangement, the tongue or key 708 maintains proper rotational alignment between the insertion tool 700 and the catheter 30. Specifically, the tongue or key 708 maintains alignment between the bottom opening 716 of the funnel lumen 710 and the guide wire lumen 42/43 of the catheter 30 such that the guide wire 36 is automatically aligned with the guide wire lumen 42/43 upon insertion into the top opening 714 of the funnel lumen 710. Similar to the tongue or key 608 discussed with referenced to FIG. 17B, the tongue or key 708 may be replaced by a non-round surface inside the main lumen 706 which engages a similarly sized and shaped non-round surface on the catheter shaft 38.

In preferred embodiments, the main body 702 also includes a slot or groove 712 providing access to the main lumen 706. The slot 712 extends along the length of the main body 702 and is preferably continuous with the bottom opening 716 of the funnel lumen 710. The slot 712 is sized to allow passage of a conventional guide wire 36 therethrough. The slot 712 permits the insertion tool 700 to be slid proximally along the shaft 38 of the catheter 30 while maintaining position of the guide wire 36.

The insertion tool 700 may be used substantially the same as insertion tool 600, except that the guide wire 36 is inserted into the funnel lumen 710 by way of the top opening 714. All other aspects of the use of insertion tool 700 are substantially similar to the use of insertion tool 600.

Insertion tool 700 may be made using conventional techniques such as injection molding and may be formed of any medical grade polymer such as PP, ABS, or the like. The overall length of insertion tool 700 is approximately 1.50 inches, wherein the funnel-shaped extension 704 is approximately 0.625 inches in length, and the main body portion 702 is approximately 0.875 inches in length.

The inside diameter of the main body 702 is sized to accommodate a conventional catheter 30 and, therefore, may have an inside diameter of approximately 0.100 to 0.120 inches and an outside diameter of approximately 0.262 inches tapering to 0.142 inches. Tongue or key 708 may have a width of approximately 0.020 inches and a height of approximately 0.03 inches to correspond to the size and shape of the channel 42/43. The bridge portion 720 may have a length of approximately 0.220 inches. The slot or groove 712 may have a width of approximately 0.060 inches. The top opening 714 of the funnel-shaped extension 704 may have a width of approximately 0.280 inches and the bottom opening 716 may have a width of approximately 0.060 inches corresponding to the width of the slot 712.

The funnel-shaped extension 704 may have a height of approximately 0.444 inches and a width of approximately 0.343 inches. The proximal angled surface of the funnel-shaped extension 704 may be formed at an angle of 45 degrees from vertical. The distal angled surface of the funnel-shaped extension 704 may be formed at an angle of 17.5 degrees from horizontal. The inside surfaces defining the funnel lumen 710 may be formed at an angle of approximately 30 degrees from vertical.

Refer now to FIGS. 19 and 20A, which illustrate a re-insertion tool 800 in accordance with a first embodiment of the present invention. For purposes of clarity, only the shaft 38 of the catheter 30 has been illustrated. Although not illustrated, the reinsertion tool 800 is designed for use in combination with a endoscope 502/150 having a side port 506 and a main port 504, as shown in FIG. 16. The re-insertion tool 800 is illustrated from a distal viewpoint with the endoscope in the direction indicated by arrow 802. Except as described herein with specific reference to re-insertion tool 800, catheter 30 and endoscope 502/150 are the same as described previously. In addition, it is to be understood that the re-insertion tool 800 and the catheter 30 are designed to be used in conjunction with a guide wire 36 (not shown) as described previously.

As described hereinabove, C-channel 43 has an opening or slot that is slightly larger than a slit and slightly smaller than the corresponding opening of the U-channel 42. The C-channel 43 has the advantage of containing the guide wire 36 therein while permitting easy passage of the guide wire 36 therethrough, because the opening or slot is sized to be approximately equal to or less than the outside diameter of the guide wire 36. However, although the C-channel 43 provides these advantages, problems may arise when the catheter 30 is backloaded over the guide wire 36. Depending on the size of the port of the endoscope, the guide wire 36 may not automatically re-enter in to the C-channel 43.

Specifically, because the endoscope 502/150 may be too small to accommodate the guide wire 36 and the catheter 30 side-by-side within the lumen of the endoscope, it is desirable to re-introduce the guide wire 36 into the C-channel 43 of the catheter 30 proximal of the port 504 of the endoscope 502/150. Thus, with the distal portion of the guide wire 36 disposed in the C-channel 43 of the catheter 30 distal of the port 504 of the endoscope 502/150, and the proximal portion of the guide wire 36 disposed adjacent to (i.e., side-by-side) the catheter 30 proximal of the port 504, the re-insertion tool 800 may be used to re-introduce the guide wire 36 into the C-channel 43 of the catheter 30 proximal of the port 504. By re-inserting the guide wire 36 into the C-channel 43 of the catheter 30 proximal of the port 504, the re-insertion tool 800 facilitates easy retraction and advancement of the catheter 30 and/or guide wire 36 relative to the endoscope 502/150. The re-insertion tool 800 further facilitates easy advancement and retraction of the catheter 30 independent of the guide wire 36. Further yet, the re-introduction tool 800 allows the use of catheter 30 with virtually any size endoscope 502/150.

Re-insertion tool 800 includes a series of proximal flanges 804 that are sized to be slightly larger than the inside diameter of the port 504 of the endoscope 502/150. By providing a plurality of flanges 804, the re-insertion tool 800 in sized to snugly fit in several different endoscopes having ports 504 with different inside diameters. The flanges 804 are large enough to prevent the re-insertion tool 800 from penetrating the valve or grommet disposed in the port 504 of the endoscope 502/150, thereby preventing the re-insertion tool 800 from falling into the endoscope lumen.

Re-insertion tool 800 further includes a ring portion 806 disposed distal of the flanges 804. The ring portion 806 is sized to fit inside the port 504 of the endoscope 502/150. The ring portion 806 may have a plurality of depressions or slots 808 to impart radial flexibility therein.

The ring portion 806 defines an inside lumen 810 into which the shaft 38 of the catheter 30 may be slidably disposed. A keel 812 is disposed in the lumen 810 and is preferably integrally formed with the ring portion 806. The keel 812 rides in the C-channel 43 of the catheter shaft 38. The keel serves to facilitate tracking of the reinsertion tool 800 along the shaft 38 of the catheter 30 and prevent the re-insertion tool 800 from completely sliding off the catheter 30.

The inner lumen 810 of the re-insertion tool 800 may be tapered to a larger diameter at the proximal end thereof to form a funnel shape to allow additional freedom of movement of the guide wire 36 proximal of the tool 800. In addition, the keel 812 may be tapered such that the proximal portion thereof is shorter than the distal portion thereof, which may serve to gradually push the guide wire 36 into the C-channel 43 of the shaft 38. Re-insertion tool 800 may further include a window 814 to facilitate greater freedom of movement of the guide wire 36 proximal of the re-insertion tool 800.

The re-insertion tool 800 may be made of any suitable medical grade material and may be formed by a number of different processes. For example, the re-insertion tool 800 may be formed by injection molding a polymer sold under the tradename ACETAL. The preferred dimensions of the re-insertion tool 800 are illustrated in FIGS. 20B–20G.

In use, as the catheter 30 is inserted into the port 504 of the endoscope 502/150, the re-insertion tool 800 may be slid down the shaft 38 until it engages the valve or grommet disposed in the port 504. After the guide wire 36 has been inserted into the catheter 30, the catheter 30 and the guide wire 36 may be separated proximal of the port 504 to allow for faster and easier manipulation of the catheter 30 and the guide wire 36. As the catheter 30 and/or guide wire 36 are advanced into the endoscope 502/150, the re-insertion tool 800 forces the guide wire 36 back into the C-channel 43 of the catheter shaft 38. Thus, distal of the re-insertion tool 800 and distal of the port 504, the guide wire 36 is constrained inside the C-channel 43. The re-insertion tool 800 also constrains the guide wire adjacent the valve or grommet disposed in the port 504, thereby protecting the guide wire 36 and catheter 30 and facilitating free longitudinal movement thereof relative to the valve or grommet disposed in the port 504.

Figure 21:
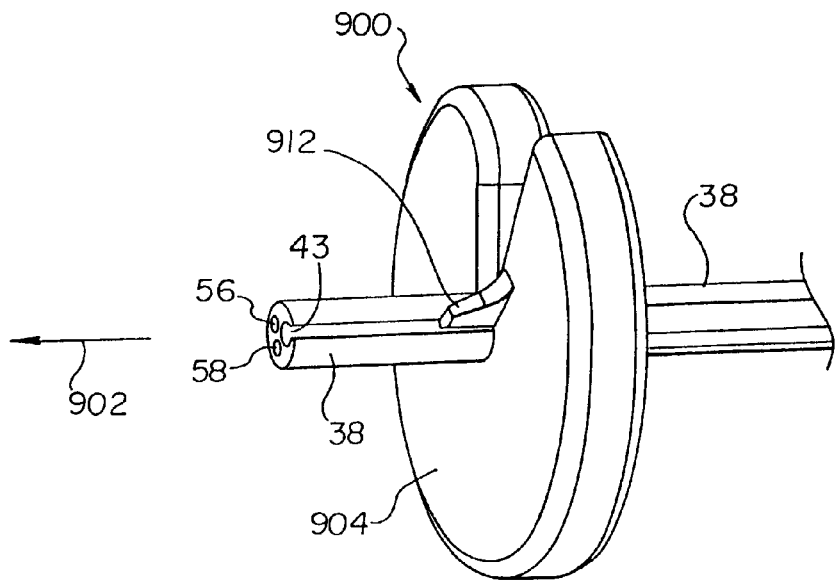
FIG. 21 is a perspective view of a re-insertion tool in accordance with a second embodiment of the present invention.

Refer now to FIG. 21, which illustrates re-insertion tool 900 in accordance with a second embodiment of the present invention. Except as described herein, re-insertion tool 900 is the same in form and function as re-insertion tool 800 described with reference to FIG. 19. A notable difference is that re-insertion tool 900 is a twist-on device that may be added or removed from the shaft 38 of the catheter 30 at any time during the procedure. Similar to the illustration of FIG. 19, re-insertion tool 900 illustrated in FIG. 21 is shown from a distal perspective, with the endoscope in the direction of arrow 902.

Re-insertion tool 900 includes a disk portion 904 having an outside diameter sized to be larger than the inside diameter of the port 504 of the endoscope 502/150. Disk portion 904 serves similar functions as flanges 804 described with reference to re-insertion tool 800. Although not shown, re-insertion tool 900 may include a ring portion disposed on the distal surface of the disk portion 904 to serve the same function as ring portion 806 described with reference to re-insertion tool 800. Re-insertion tool 900 further includes a keel 912 serving the same function as keel 812 described with reference to re-insertion tool 800.

Figure 22A:
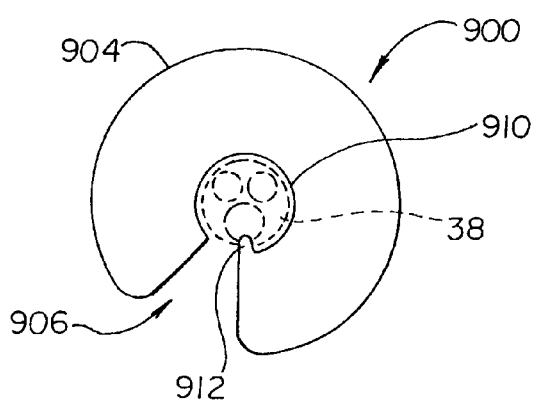
FIGS. 22A–22C are top, rear and side views, respectively, of the re-insertion tool illustrated in FIG. 21.
Figure 22B:
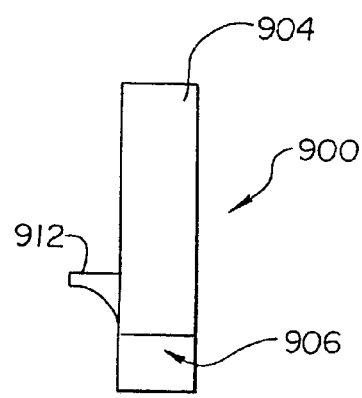
Figure 22C:
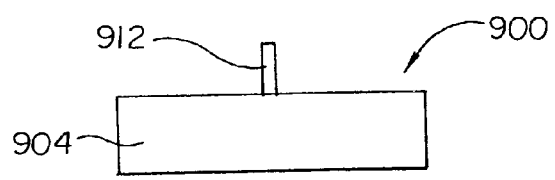

As best seen in FIG. 22A, re-insertion tool 900 includes a lumen 910 that is similarly dimensioned and serves the same function as lumen 810 described with reference to re-insertion tool 800. For purposes of illustration only, the shaft 38 of the catheter is shown in phantom in FIG. 22A. Re-insertion tool 900 further includes a window or slot 906 arranged perpendicular to the lumen 910. Preferably, the window 906 has an angular opening of 45 degrees. The slot or window 906 allows the re-insertion tool 900 to be loaded from the side onto the shaft 38 of the catheter 30. Once the shaft 38 is disposed in the lumen 910 with the keel 912 aligned with the C-channel 43, the re-insertion tool 900 may be locked in place by rotating the tool 900 90 degrees. Other than the side loading and locking feature of re-insertion tool 900, the use of re-insertion tool 900 is the same as the use of re-insertion tool 800.

A further embodiment, although not illustrated, of a re-insertion tool is contemplated comprising a "T" shaped device that is attached to and penetrates the valve or grommet in the port 504 of the endoscope 502/150 and allows a catheter 30 and guide wire 36 system to pass through a restrictive lumen disposed in the device. The restrictive lumen would allow just enough space for the catheter 30 to pass therethrough such that as the catheter 30 and the guide wire 36 are pushed through the restrictive lumen simultaneously, the guide wire 36 is forced into the C-channel 43 of the catheter 30 substantially the same as describe above. The "T" shaped device may also have a slot running parallel to the restrictive lumen. The slot may be deep and wide enough to allow the guide wire 36 to pass therethrough, thus allowing the removal of the re-insertion device and/or the catheter 30 once the guide wire 36 has been positioned.

It is further contemplated that any of the re-insertion tools described herein may further include a locking mechanism. The locking mechanism may be secured to the port 504 of the endoscope 502/150 or may be secured to the shaft 38 of the catheter 30. With either arrangement, the guide wire 36 is automatically re-introduced into the C-channel 43 of the shaft 38.

From the foregoing, it is apparent that new and useful insertion and re-insertion tools have been described. The insertion tools provide a method for easily inserting a guide wire into a guide wire lumen of a catheter, particularly a rapid exchange catheter, for use in an endoscope. The re-insertion tools facilitate easy advancement of the catheter and/or guide wire into the side port of the endoscope. Those skilled in the art will recognize that the present invention may be manifested in a wide variety of forms other than the specific embodiments contemplated and described herein. Accordingly, departures in form and detail may be made without departing from the scope and spirit of the present invention as described in the appended claims.

What is claimed is:

1. An insertion tool for use in inserting a guide wire into a guide wire lumen of a catheter for use in a lumen of an endoscope, the insertion tool comprising:
    a main body having a first opening, a second opening, and a main lumen extending therethrough, the main lumen sized to accommodate the catheter therein, and
    a funnel-shaped extension connected to and disposed adjacent to the main body, the funnel-shaped extension having a proximal opening and a funnel lumen extending therethrough, wherein the funnel lumen has a distal end, the proximal opening sized larger than the guide wire, the distal end of the funnel lumen positioned and sized to communicate with the guide wire lumen of the catheter when the catheter is disposed in the main lumen such that the guide wire may be easily inserted into the proximal opening of the funnel lumen and into the guide wire lumen of the catheter, wherein the main body and the funnel-shaped extension each includes a distal portion, and wherein the distal portion of the funnel-shaped extension merges with the distal portion of the main body to define a merged section, the merged section sized to fit in the lumen of the endoscope.

2. An insertion tool as in claim 1, wherein the insertion tool is adapted for use with a catheter having a longitudinal slot providing access to the guide wire lumen, the insertion tool further comprising a means for maintaining alignment between the funnel lumen and the slot of the catheter.

3. An insertion tool as in claim 2, wherein the alignment means comprises a tongue.

4. An insertion tool as in claim 2, wherein the alignment means comprises a non-round surface.

5. An insertion tool as in claim 2, wherein the main body is sized to fit in the lumen of the endoscope.

6. An insertion tool for use in inserting a guide wire into a guide wire lumen of a catheter for use in a lumen of an endoscope, the insertion tool comprising;

a main body having a first opening, a second opening, and a main lumen extending therethrough, the main lumen sized to accommodate the catheter therein; and a funnel-shaped extension integrally formed with and disposed adjacent to the main body, the funnel-shaped extension having a proximal opening and a funnel lumen extending therethrough, the funnel lumen having a distal end merging with the main lumen, the proximal opening being larger than the guide wire and the distal end of the funnel lumen aligned with the guide wire lumen of the catheter, such that, when the catheter is disposed in the main lumen, the guide wire may be easily inserted into the proximal opening of the funnel lumen and into the guidewire lumen of the catheter, wherein the main body and the funnel-shaped extension each include a distal portion, and wherein the distal portion of the funnel-shaped extension merges with the distal portion of the main body to define a merged section, the merged section sized to fit in the lumen of the endoscope.

7. An insertion tool as in claim 6, wherein the insertion tool is adapted for use with a catheter having a longitudinal slot providing access to the guide wire lumen, the insertion tool further comprising a tongue disposed in the main lumen, the tongue sized to fit in the slot of the catheter such that the tongue maintains alignment between the funnel lumen and the slot of the catheter.

8. An insertion tool as in claim 6, wherein the insertion tool is adapted for use with a catheter having a longitudinal slot providing access to the guide wire lumen, the insertion tool further comprising a non-round surface in the main lumen, the non-round surface engaging a non-round surface extending along a portion of the catheter such that the engaging surfaces maintain alignment between the funnel lumen and the slot of the catheter.

9. An insertion tool as in claim 6, further comprising a longitudinal slot in the main body to allow removal of the guide wire from the insertion tool while the guide wire remains disposed in the guide wire lumen of the catheter.

10. An insertion tool as in claim 6, further comprising a longitudinal slot in the funnel-shaped extension to allow removal of the guide wire from the insertion tool while the guide wire remains disposed in the guide wire lumen of the catheter.

11. An insertion tool as in claim 6, wherein the insertion tool is adapted for use with a catheter having a longitudinal slot providing access to the guide wire lumen, the insertion tool further comprising a means for maintaining alignment between the funnel lumen and the slot of the catheter.

* * * * *